(12) United States Patent
Kakkis et al.

(10) Patent No.: US 10,457,701 B2
(45) Date of Patent: *Oct. 29, 2019

(54) SIALIC ACID ANALOGS

(71) Applicant: Ultragenyx Pharmaceutical Inc., Novato, CA (US)

(72) Inventors: Emil Kakkis, Novato, CA (US); Steven Jungles, Novato, CA (US); He Zhao, Madison, CT (US)

(73) Assignee: Ultragenyx Pharmaceutical Inc., Novato, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/050,343

(22) Filed: Jul. 31, 2018

(65) Prior Publication Data

US 2019/0127409 A1    May 2, 2019

Related U.S. Application Data

(63) Continuation of application No. 14/944,779, filed on Nov. 18, 2015, now Pat. No. 10,065,981, which is a continuation of application No. 14/461,295, filed on Aug. 15, 2014, now Pat. No. 9,221,858, which is a continuation of application No. 13/659,550, filed on Oct. 24, 2012, now Pat. No. 8,840,926.

(60) Provisional application No. 61/550,610, filed on Oct. 24, 2011.

(51) Int. Cl.
| | |
|---|---|
| *C07H 7/02* | (2006.01) |
| *C07H 13/10* | (2006.01) |
| *C07D 493/08* | (2006.01) |
| *C07H 7/027* | (2006.01) |
| *C07H 13/04* | (2006.01) |

(52) U.S. Cl.
CPC ............ *C07H 7/02* (2013.01); *C07D 493/08* (2013.01); *C07H 7/027* (2013.01); *C07H 13/04* (2013.01); *C07H 13/10* (2013.01)

(58) Field of Classification Search
None
See application file for complete search history.

(56) References Cited

U.S. PATENT DOCUMENTS

| | | | |
|---|---|---|---|
| 4,698,332 | A | 10/1987 | Ogasawara et al. |
| 5,624,677 | A | 4/1997 | El-Rashidy et al. |
| 5,747,475 | A | 5/1998 | Nordquist et al. |
| 6,156,544 | A | 12/2000 | Dawson et al. |
| 6,444,649 | B1 | 9/2002 | Inamori et al. |
| 8,524,772 | B2 | 9/2013 | Arad et al. |
| 8,840,926 | B2 | 9/2014 | Kakkis et al. |
| 9,221,858 | B2 | 12/2015 | Kakkis et al. |
| 9,241,896 | B2 | 1/2016 | Kakkis |
| 9,511,015 | B2 | 12/2016 | Kakkis |
| 9,554,987 | B2 | 1/2017 | Kakkis |
| 10,065,981 | B2 | 9/2018 | Kakkis et al. |
| 2004/0192642 | A1 | 9/2004 | Yang et al. |
| 2008/0085306 | A1 | 4/2008 | Nangia et al. |
| 2008/0260824 | A1 | 10/2008 | Nangia et al. |
| 2010/0159001 | A1 | 6/2010 | Cardinal et al. |
| 2010/0160363 | A1 | 6/2010 | Cardinal et al. |
| 2010/0226855 | A1 | 9/2010 | Nangia et al. |
| 2012/0264928 | A1 | 10/2012 | Noguchi et al. |
| 2013/0225513 | A1 | 8/2013 | Kakkis |
| 2013/0273160 | A1 | 10/2013 | Kakkis |
| 2016/0297846 | A1 | 10/2016 | Kakkis et al. |
| 2017/0073366 | A1 | 3/2017 | Klopp et al. |
| 2017/0136051 | A1 | 5/2017 | Kakkis |
| 2017/0157160 | A1 | 6/2017 | Kakkis |

FOREIGN PATENT DOCUMENTS

| | | |
|---|---|---|
| EP | 2332552 | 6/2011 |
| EP | 2593109 | 5/2013 |
| JP | S63-139193 | 6/1988 |
| JP | 2010-529021 | 8/2010 |
| KR | 10-2001-0042603 | 5/2001 |
| WO | WO 1999/052931 | 10/1999 |
| WO | WO 2004/000366 | 12/2003 |
| WO | WO 2006/096161 | 9/2006 |
| WO | WO 2008/150477 | 12/2008 |
| WO | WO 2009/032605 | 3/2009 |
| WO | WO 2010/080580 A2 | 7/2010 |
| WO | WO 2010/131712 | 11/2010 |
| WO | WO 2012/009474 | 1/2012 |
| WO | WO 2013/063149 | 5/2013 |
| WO | WO 2013/109906 | 7/2013 |
| WO | WO 2016/121810 | 8/2016 |
| WO | WO 2017/048817 | 3/2017 |

OTHER PUBLICATIONS

Supplementary European Search Report for European Application No. 12843460.2, dated Aug. 12, 2015, 13 pages.
Supplementary Partial European Search Report for European Application No. 12843460.2, dated Feb. 25, 2015, 6 pages.
International Preliminary Report on Patentability for International Application No. PCT/US2012/061737, dated Apr. 29, 2014, 9 pages.
International Search Report and Written Opinion for International Application No. PCT/US2012/061737, dated Mar. 15, 2013, 13 pages.
Supplementary European Search Report for European Application No. 11807478.0, dated Dec. 5, 2013, 5 pages.
International Preliminary Report on Patentability for International Application No. PCT/US2011/043910, dated Jan. 15, 2013, 8 pages.
International Search Report and Written Opinion for International Application No. PCT/US2011/043910, dated Oct. 18, 2011, 10 pages.
Supplementary European Search Report for European Application No. 13739040.7, dated Aug. 4, 2015, 8 pages.
International Preliminary Report on Patentability for International Application No. PCT/US2013/022167, dated Jul. 22, 2014, 4 pages.

(Continued)

Primary Examiner — Robert A Wax
Assistant Examiner — Danah Al-Awadi
(74) Attorney, Agent, or Firm — Cooley LLP

(57) ABSTRACT

The present invention provides sialic acid analogs and their compositions useful for the treatment of sialic acid deficiencies.

15 Claims, 12 Drawing Sheets

(56) References Cited

OTHER PUBLICATIONS

International Search Report and Written Opinion for International Application No. PCT/US2016/051694, dated Dec. 30, 2016, 9 pages.
Aich, U. et al, "Development of delivery methods for carbohydrate-based drugs: controlled release of biologically-active short chain fatty acid-hexosamine analogs," Glycoconjugate Journal, 27(4):445-459 (May 2010). doi: 10.1007/s10719-010-9292-3. Epub May 11, 2010.
Allevi, P. et al., "Chemoselective synthesis of sialic acid 1,7-lactones," J. Org. Chem., 75(16):5542-5548 (2010).
Argov, Z. et al., "Hereditary inclusion body myopathy. The Middle Eastern genetic cluster," Neurology, 60(9):1519-1523 (2003).
Askanas, V. et al., "Sporadic inclusion-body myositis and hereditary inclusion-body myopathies: current concepts of diagnosis and pathogenesis," Curr. Opin. Rheumatol., 10(6):530-542 (1998).
Broccolini, A. et al., "Novel GNE mutations in Italian families with autosomal recessive hereditary inclusion-body myopathy," Human Mutation, 23(6):632 (2004).
CAS Registry No. 1053644-78-2; STN Entry Date Sep. 28, 2008.
Colombo, R. et al., "The first synthesis of N-acetylneuraminic acid 1,7-lactone," Chem. Commun., 43:5517-5519 (2008).
Cornforth, J. W. et al., "The synthesis of N-Acetylneuraminic acid," Biochemical Journal, 68(1):57-61 (Jan. 1958).
Dufner, G. et al., "Base- and Sugar-Modified Cytidine Monophosphate N-Acetylneuraminic Acid (CMP-Neu5Ac) Analogues—Synthesis and Studies with α(2-6)-Sialyltransferase from Rat Liver," European Journal of Organic Chemistry, 2000(8):1467-1482 (Apr. 2000).
Eisenberg, I. et al., "The UDP-N-acetylglucosamine 2-epimerase/N-acetylmannosamine kinase gene is mutated in recessive hereditary inclusion body myopathy," Nat. Genet., 29(1):83-87 (2001).
Fuchidori Kuuhou wo tomonau enigata myopathy no konponteki no konponteki chiryouhou kaihatu [Development of fundamental therapy of distal therapy of distal type myopathy involving rimmed vacuole rimmed vacuole], Heiesei-19 generalization allotment study report, Apr. 2008, pp. 1-7 (with English translation of relevant portion), 9 pages.
Frost, R. A. et al., "Regulation of insulin-like growth factor-I in skeletal muscle and muscle cells," Minerva Endocrinol., 28(1):53-73 (2003).
Galeano, B. et al., "Mutation in the key enzyme of sialic acid biosynthesis causes severe glomerular proteinuria and is rescued by N-acetylmannosamine," The Journal of Clinical Investigation, 117(6):1585-1594 (2007).
Gavezzotti, A., "Are Crystal Structures Predictable?", Accounts of Chemical Research, 27:309-314 (1994).
Horn, E. J. et al., "Investigation into an efficient synthesis of 2,3-dehydro-N-acetyl neuraminic acid leads to three decarboxylated sialic acid dimers," Carbohydrate Research, 343(5):936-940 (2008).
Jay, C. M. et al., "Hereditary Inclusion Body Myopathy (HIBM2)," Gene Regulation and Systems Biology, 3:181-190 (2009).
Liu, J. L-C et al., "Overproduction of CMP-Sialic Acid Synthetase for Organic Synthesis," J. Am. Chem. Soc., 114(10):3901-3910 (1992).
Malicdan, M. C. V. et al., "Prophylactic treatment with sialic acid metabolites precludes the development of the myopathic phenotype in the DMRV-hIBM mouse model," Nature Medicine, 15(6):690-695 (2009).
Martin, R. et al., "The synthesis and enzymatic incorporation of sialic acid derivatives for use as tools to study the structure, activity, and inhibition of glycoproteins and other glycoconjugates," Bioorganic & Medicinal Chemistry, 6(8):1283-1292 (1998).
Nishino, I. et al., "Distal myopathy with rimmed vacuoles is allelic to hereditary inclusion body myopathy," Neurology, 59:1689-1693 (2002).
Nishino, I. et al., "Muscular dystrophies," Current Opinion in Neurology, 15:539-544 (2002).
Nishino, I., "Development of a Fundamental Therapy for Distal Myopathy with Rimmed Vacuoles," Research Report Summary, Heisei 19 Soukatsu / Buntan Kenkyu Houkokusho, pp. 1-7 (2008) (with English Abstract).
Noguchi, S. et al., "Reduction of UDP-N-acetylglucosamine 2-Epimerase/N-Acetylmannosamine Kinase Activity and Sialylation in Distal Myopathy with Rimmed Vacuoles," The Journal of Biological Chemistry, 279(12):11402-11407 (2004).
Oetke, C. et al., "Evidence for efficient uptake and incorporation of sialic acid by eukaryotic cells," European Journal of Biochemistry, 268(16):4553-4561 (2001).
Oetke, C. et al., "Versatile Biosynthetic Engineering of Sialic Acid in Living Cells Using Synthetic Sialic Acid Analogues," The Journal of Biological Chemistry, 277(8):6688-6695 (2002).
Penner, J. et al., "Influence of UDP-GlcNAc 2-Epimerase/ManNAc Kinase Mutant Proteins on Hereditary Inclusion Body Myopathy," Biochemistry, 45(9):2968-2977 (2006).
Pubchem Compound Database, CID 440962, "N-acetylneuraminate 9-phosphate," Created on Jun. 24, 2005, 5 pages.
Rezende, M. C. et al., "A facile route to 9-phosphorylated neuraminic acid derivatives," Synthetic Communications, 28(23):4393-4400 (1998).
Ricci, E. et al., "NCAM is hyposialylated in hereditary inclusion body myopathy due to GNE mutations," Neurology, 66:755-758 (2006).
Rota, P. et al., "General and chemoselective N-transacylation of secondary amides by means of perfluorinated anhydrides," Angewandte Chemie International Edition, 49(10):1850-1853 (2010).
Sato, S. et al., "Studies on sialic acids. XIV. Lactone derivatives of N-Acetylneuraminic acid," Chemical & Pharmaceutical Bulletin, 36(12):4678-4688 (1988).
Seppala, R. et al., "Mutations in the Human UDP-N-Acetylglucosamine 2-Epimerase Gene Define the Disease Sialuria and the Allosteric Site of the Enzyme," Am. J. Hum. Genet., 64:1563-1569 (1999).
Scheinthal, B. M. et al., "Multiple forms of sialic acids," Carbohydrate Research, 6:257-265 (1968).
Sparks, S. E. et al., "Use of a cell-free system to determine UDP-N-acetylglucosamine 2-epimerase and N-acetylmannosamine kinase activities in human hereditary inclusion body myopathy," Glycobiology, 15(11):1102-1110 (2005).
Vippagunta, S. R. et al., "Crystalline Solids," Advanced Drug Delivery Reviews, 48:3-26 (2001).
Wajnrajch, M. P., "Physiological and Pathological Growth Hormone Secretion," Journal of Pediatric Endocrinology & Metabolism, 18(4):325-338 (2005).
Yao, R. (ed.), Polymers for Pharmaceuticals, Second Edition, Chemistry Industry Press, Mar. 2008, pp. 76-87 (with English translation of relevant portion).
ClinicalTrials.gov, "A Phase 1 Study to Evaluate the Safety and Pharmacokinetics of Single and Repeat Doses of Sialic Acid Extended Release (SA-ER) Tables in Patients With Hereditary Inclusion Body Myopathy (HIBM)", NCT01359319, ClinicalTrials.gov [Online], First Received: May 20, 2011. Retrieved from the Internet: <URL: https://clinicaltrials.gov/ct2/show/NCT01359319>, 6 pages.
ClinicalTrials.gov, "Pharmacokinetic Study on N-acetylneuraminic Acid in Patients With Distal Myopathy With Rimmed Vacuoles (DMRV)—Hereditary Inclusion Body Myopathy (hIBM)", NCT01236898, ClinicalTrials.gov [Online], First Received: Nov. 8, 2010. Retrieved from the Internet: <URL: https://clinicaltrials.gov/ct2/show/NCT01236898>, 4 pages.

SIALIC ACID ANALOGS

CROSS-REFERENCE TO RELATED APPLICATION

This application is a continuation of U.S. patent application Ser. No. 14/944,779 filed Nov. 18, 2015, which is a continuation of U.S. patent application Ser. No. 14/461,295 filed Aug. 15, 2014, now U.S. Pat. No. 9,221,858, which is a continuation of U.S. patent application Ser. No. 13/659,550 filed Oct. 24, 2012, now U.S. Pat. No. 8,840,926, which claims priority to U.S. Provisional Application No. 61/550,610 filed Oct. 24, 2011, the disclosure of each of which is herein incorporated by reference in its entirety for all purposes.

FIELD OF THE INVENTION

The present invention relates to sialic acid analogs useful for treating a sialic acid deficiency.

BACKGROUND OF THE INVENTION

Sialic acid generally refers to the N- or O-substituted derivatives of neuraminic acid, a monosaccharide with a nine-carbon backbone. The most common member of this group is N-acetylneuraminic acid (also known as Neu5Ac or NANA) and thereby the term "sialic acid" is often used as the name of N-acetylneuraminic acid. It is the only sugar that contains a net negative charge and is typically found on terminating branches of N-glycans, O-glycans, and glycosphingolipids (gangliosides) (and occasionally capping side chains of GPI anchors). The sialic acid modification of cell surface molecules is crucial for many biological phenomena including protein structure and stability, regulation of cell adhesion, and signal transduction. Thus, sialic acid abnormalities, such as sialic acid deficiency, can cause severe health problems. Sialic acid deficiency disorders, such as Hereditary Inclusion Body Myopathy (HIBM or HIBM type 2), Nonaka myopathy, Distal Myopathy with Rimmed Vacuoles (DMRV) and most recently renamed GNE myopathy are a clinical disease resulting from a reduction in sialic acid production.

The biosynthesis steps and feedback regulation of GNE/MNK is depicted in FIG. 1. The production of sialic acid on glycoconjugates requires the conversion of N-acetylglucosamine (conjugated to its carrier nucleotide sugar UDP) to sialic acid. The sialic acid subsequently enters the nucleus where it is conjugated with its nucleotide sugar carrier CMP to make CMP-sialic acid, which is used as a donor sugar for glycosylation reactions in the cell. CMP-sialic acid is a known regulator of GNE/MNK activity. Jay et al., *Gene Reg. & Sys. Biol.* 3:181-190 (2009). Patients with HIBM have a deficiency in the production of sialic acid via the rate controlling enzyme GNE/MNK, which conducts the first two steps of this sequence: 1) epimerization of the glucosamine moiety to mannosamine with release of UDP, and 2) phosphorylation of the N-acetylmannosamine. The mutations causing HIBM occur in the regions encoding either the epimerase domain (GNE) or the kinase domain (MNK). Nearly twenty GNE mutations have been reported in HIBM patients from different ethnic backgrounds with founder effects among the Iranian Jews and Japanese. Broccolini et al., *Hum. Mutat.* 23:632 (2004). Most are missense mutations and result in decreased enzyme GNE activity and underproduction of sialic acid. Sparks et al., *Glycobiology* 15(11):1102-10 (2005); Penner et al., *Biochemistry* 45:2968-2977 (2006).

Researchers have investigated the use of sialic acid in substrate replacement therapy for treating sialic acid deficiency disorders and achieved some promising results in the preliminary studies.

SUMMARY OF THE INVENTION

The present invention provides novel sialic acid analogs useful for treating any sialic acid deficiency disorders and methods of treating and preventing sialic acid deficiencies utilizing the present compounds and the pharmaceutical compositions or formulations thereof.

In one embodiment, the present application provides a compound having structural Formula (I):

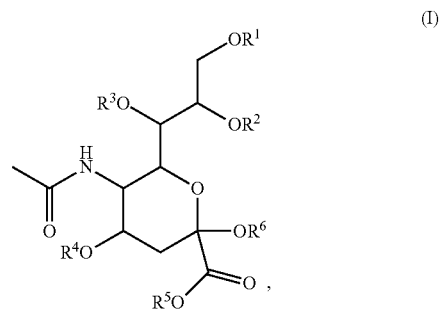

or a pharmaceutically acceptable salt or solvate thereof; wherein:

$R^2$, $R^3$, $R^4$, and $R^6$ are independently hydrogen or a moiety selected from structural formula (a), (b), (c), (d), (e), (f), and (g):

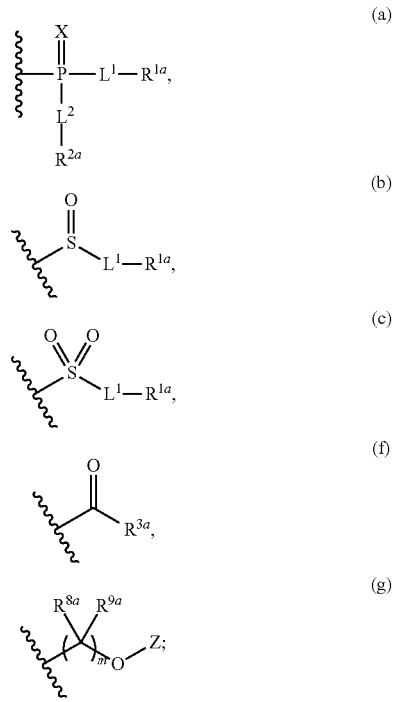

$R^1$ is a moiety selected from structural formula (a), (b), (c), (f), and (g); or a nucleoside phosphate moiety;

X is oxygen or sulfur;

$L^1$ and $L^2$ are each independently a covalent bond, —O—, or —$NR^{10a}$—;

$R^{10a}$ is hydrogen or optionally substituted alkyl;

$R^{1a}$ and $R^{2a}$ are each independently hydrogen, optionally substituted alkyl, optionally substituted heteroalkyl, optionally substituted aryl, optionally substituted heteroaryl, optionally substituted carbocyclyl, optionally substituted heterocyclyl, —$X^a$—C(O)—O—$R^{11a}$, or —$X^a$—O—C(O)—O—$R^{11a}$;

$X^a$ is optionally substituted alkylene;

each $R^{11a}$ is independently hydrogen, optionally substituted alkyl, or optionally substituted heteroalkyl;

$R^{3a}$ is optionally substituted alkyl; or alternatively, $R^{3a}$, together with the carboxyl moiety to which it is attached, form a monopeptidyl or dipeptidyl group;

each $R^{8a}$ and $R^{9a}$ is independently hydrogen or optionally substituted alkyl;

m is 1 or 2;

Z is hydrogen, lower alkyl, an amide group, a lactam group, an ester group, a lactone group, an urea group, a cyclic urea group, a carbonate group, a cyclic carbonate group, a carbamate group, a cyclic carbamate group, or a moiety selected from (a), (b), (c), and (f);

$R^5$ is hydrogen, $G^+$, optionally substituted alkyl, or a moiety selected from (a), (b), (c), (f), and (g); and $G^+$ is a charged organic amine moiety; or alternatively, $OR^3$ and $OR^6$ are taken together to form a lactone structure represented by Formula (Ia):

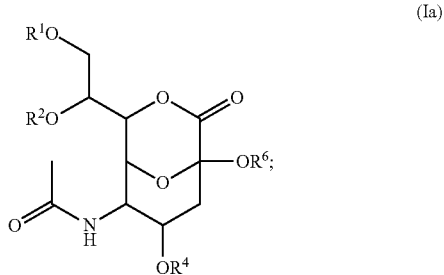

(Ia)

and with the following provisos:

(a) at least one of $R^1$, $R^2$, $R^3$, $R^4$, $R^5$, and $R^6$ is not H; and (b) $R^{3a}$ is not optionally substituted alkyl unless (1) $OR^3$ and $OR^6$ are taken together to form a lactone structure of Formula (Ia), or (2) $R^5$ is (f).

In another embodiment, the present invention provides a pharmaceutical composition comprising a compound of the present invention, or a pharmaceutically acceptable salt or solvate thereof, and a pharmaceutically acceptable carrier.

In yet another embodiment, the present invention provides a sustained release pharmaceutical composition comprising a compound of the present invention, or a pharmaceutically acceptable salt or solvate thereof, wherein the release of the compound is over a period of about four hours or more.

In yet another embodiment, the present invention provides a sustained release pharmaceutical composition comprising a compound of the present invention, or a pharmaceutically acceptable salt or solvate thereof, wherein the pharmacological effect from the compound lasts about four hours or more upon administration of the composition.

In yet another embodiment, the present invention provides a sustained release pharmaceutical composition comprising a compound of the present invention, or a pharmaceutically acceptable salt or solvate thereof; wherein the composition, upon administration, provides a therapeutically effective amount of the compound for about 4 hours or more.

In one embodiment, the present invention provides a method for treating a sialic acid deficiency in a patient in need thereof comprising administering an effective amount of a compound of the present invention, or a pharmaceutically acceptable salt or solvate thereof.

In another embodiment, the present invention provides a method for treating a sialic acid deficiency in a patient in need thereof comprising administering a compound of the present invention, or a pharmaceutically acceptable salt or solvate thereof; wherein upon administration, the compound, or a pharmaceutically acceptable salt or solvate thereof, continuously provides a therapeutically effective amount of sialic acid for about 4 hours to about 24 hours.

DETAILED DESCRIPTIONS OF THE INVENTION

Figure 1:
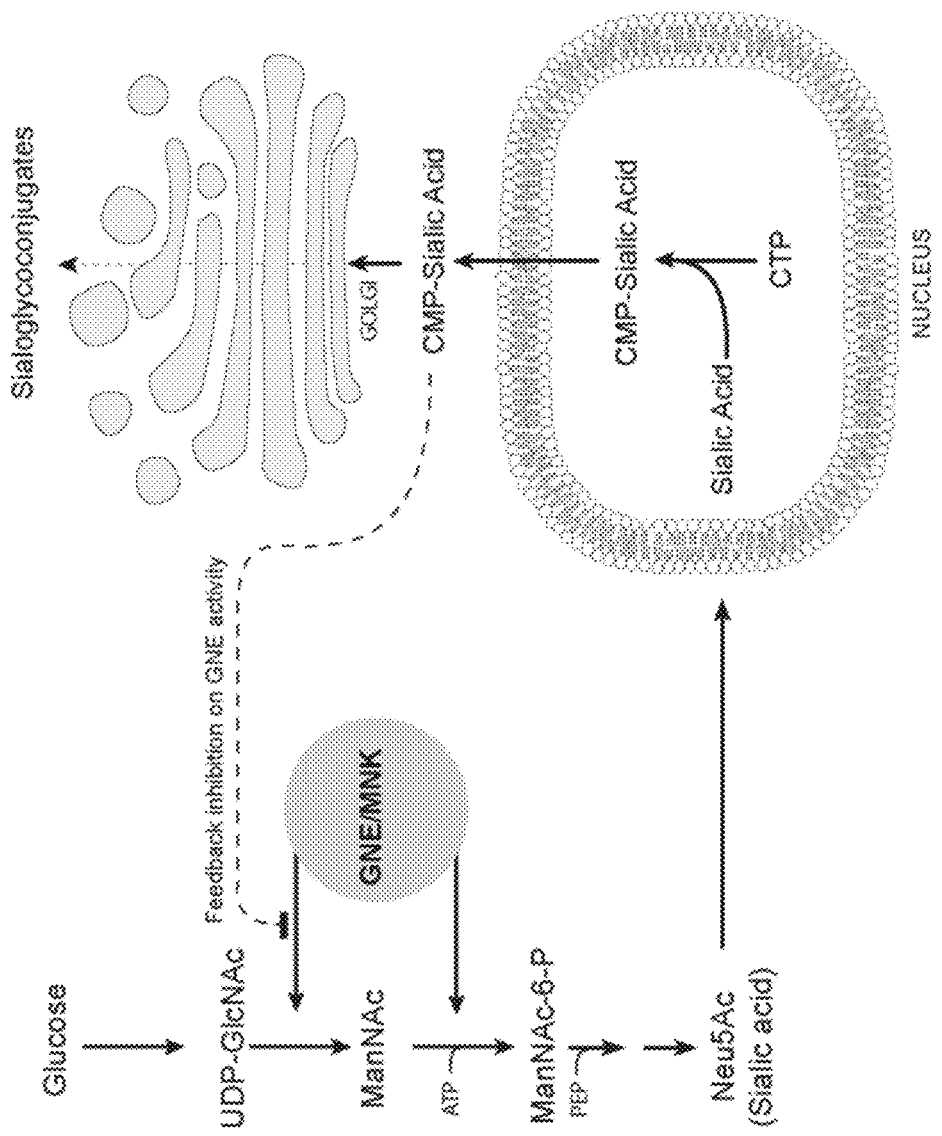
FIG. 1 shows the biosynthetic pathway of sialic acid in its subcellular locations.

Various embodiments and advantages of the present invention will be set forth in part in the description that follows, and in part will be obvious from the description, or may be learned by practice of the invention. It is to be understood that both the foregoing general description and the following detailed description are exemplary and explanatory only and are not restrictive of the invention as described.

Definitions

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

Reference to "about" a value or parameter herein includes (and describes) variations that are directed to that value or parameter per se. For example, description referring to "about X" includes description of "X".

The term "present compound(s)" or "compound(s) of the present invention" refers to compounds encompassed by structural formulae disclosed herein and includes any subgenus and specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule. The term "tautomer" as used herein refers to isomers that change into one another with great ease so that they can exist together in equilibrium.

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes "cycloakyl" as defined herein below. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). $C_1$-$C_6$ alkyl is also known as "lower alkyl".

It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. In some embodiments, an alkylene group comprises from 1 to 20 carbon atoms ($C_1$-$C_{20}$ alkylene). In other embodiments, an alkylene group comprises from 1 to 10 carbon atoms ($C_1$-$C_{10}$ alkylene). In still other embodiments, an alkylene group comprises from 1 to 6 carbon atoms ($C_1$-$C_6$ alkylene).

"Alkenyl," by itself or as part of another substituent, refers to an unsaturated branched, straight-chain or cyclic monovalent hydrocarbon radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl , but-2-en-1-yl, but-2-en-2-yl, buta-1,3 -dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —C(O)$R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. That is, arylakyl can also be considered as an alkyl substituted by aryl. Typical arylalkyl groups include, but are not limited to, benzyl, 2-phenylethan-1-yl, 2-phenylethen-1-yl, naphthylmethyl, 2-napthylethan-1-yl, 2-naphtylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_{15}$) alkyl and the aryl moiety is ($C_6$-$C_{10}$) aryl.

"Carbocyclic," or "Carbocyclyl," by itself or as part of another substituent, refers to a saturated or partially saturated, buy not aromatic, cyclic monovalent hydrocarbon radical, including cycloalkyl, cycloalkenyl, and cycloalkynyl as defined herein. Typical carbocyclyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The carbocyclyl may be further substituted by one or more heteroatoms including, but not limited to, N, P, O, S, and Si, which attach to the carbon atoms of the cycloalkyl via monovalent or multivalent bond.

"Heteroalkyl," by themselves or as part of other substituents, refer to alkyl groups, in which one or more of the carbon atoms, are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl group. Typical heteroatomic groups which can be included in these groups include, but are not limited to, —O—, —S—, —N—, —O—O—, —S—S—, —O—S—, —NR$^{201}$R$^{202}$—, =N—N—, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heterocyclic," or "Heterocyclyl,"by itself or as part of another sub stituent, refers to a carbocyclic radical in which one or more carbon atoms are independently replaced with the same or different heteroatom. The heterocyclyl may be further substituted by one or more heteroatoms including, but not limited to, N, P, O, S, and Si, which attach to the carbon atoms of the heterocyclyl via monovalent or multivalent bond. Typical heteroatoms to replace the carbon atom(s) include, but are not limited to, N, P, O, S, Si, etc. Typical heterocyclyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the heterocyclyl group comprises from 3 to 10 ring atoms (3-10 membered heterocyclyl) In other embodiments, the heterocyclyl group comprise from 5 to 7 ring atoms (5-7 membered heterocyclyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "heterocyclyl." A heterocyclyl group may be attached to the remainder of the molecule via a ring carbon atom or a ring heteroatom. "Halo," by itself or as part of another sub stituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine. "Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

An "amide" refers to an organic compound that contains the functional group consisting of a carbonyl group linked to a nitrogen atom. For example, an amide group can be represented by the following structural formula:

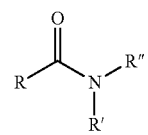

R is an optionally substituted hydrocarbon moiety;
R' and R" are independently hydrogen or optionally substituted hydrocarbon moiety.

A "lactam" group is a cyclic amide. That is, a lactam is an amide with the above structural formula where R and R' or R and R", taken together with the carbon and nitrogen atoms to which they are attached, form an optionally substituted cyclic group.

An "ester" refers to an organic compound derived by reacting/condensing an oxoacid with a hydroxyl compound. For example, an amide group can be represented by the following structural formula:

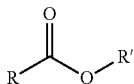

R and R' are independently hydrogen or optionally substituted hydrocarbon moiety.

A "lactone" group is a cyclic ester. That is, a lactone is an ester with the above structural formula where R and R', taken together with the carbon and oxygen atoms to which they are attached, form an optionally substituted cyclic group which can be saturated, unsaturated, or aromatic.

A "urea" or "carbamide" refers to an organic compound having the following structural formula:

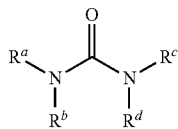

$R^a$, $R^b$, $R^c$, and $R^d$ are independently hydrogen or optionally substituted hydrocarbon moiety.

A cyclic urea is a urea with the above structural formula where any two of $R^a$, $R^b$, $R^c$, and $R^d$, taken together with the carbon and nitrogen atoms to which they are attached, form an optionally substituted cyclic group which can be saturated, unsaturated, or aromatic.

A "carbonate" refers to an organic compound having the following structural formula:

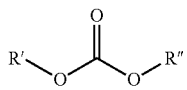

R' and R" are independently hydrogen or optionally substituted hydrocarbon moiety.

A cyclic carbonate is a carbonate with the above structural formula where R' and R", taken together with the carbon and oxygen atoms to which they are attached, form an optionally substituted cyclic group which can be saturated, unsaturated, or aromatic.

A "carbamate" refers to an organic compound having the following structural formula:

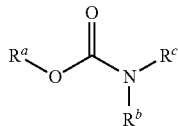

$R^a$, $R^b$, and $R^c$ are independently hydrogen or optionally substituted hydrocarbon moiety.

A cyclic carbamate is a carbamate with the above structural formula where any two of $R^a$ and $R^b$, or $R^a$ and $R^c$, taken together with the carbon and nitrogen/oxygen atoms to which they are attached, form an optionally substituted cyclic group which can be saturated, unsaturated, or aromatic.

"Hydrocarbon" refers to an organic compound consisting of hydrogen and carbon. Hydrocarbons can be straight, branched, or cyclic; and include arenes, alkanes, alkenes, cycloalkanes, alkynes, and etc. The term "substituted hydrocarbon" refers to a hydrocarbon where a carbon or hydrogen atom is replaced by an atom which is not carbon or hydrogen. The substituted hydrocarbons include substituted arenes, substituted alkanes, heteroalkanes, substituted alkenes, heteroalkenes, substituted cycloalkanes, heterocycloalkanes, substituted alkynes, and etc.

"Prodrug" refers to an inactive derivative of a therapeutically active agent that will be converted to the active agent in vivo. That is, a prodrug is a precursor of a drug.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2nd ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitroveratryloxycarbonyl ("NVOC") and the like. Representative hydroxyl protecting groups include, but are not limited to, those where the hydroxyl group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N=O$ or $R_3N\rightarrow O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =$O$, —$OR^b$, —$SR^b$, —$S^-$, =$S$, —$NR^cR^c$, =$NR^b$, =$N$—$OR^b$, trihalomethyl, —$CF_3$, —$CN$, —$OCN$, —$SCN$, —$NO$, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—$C(O)$—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —$CN$, —$OCN$, —$SCN$, —$NO$, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —$CN$, —$NO$, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. Substituent groups from the above lists useful for substituting other specified groups or atoms will be apparent to those of skill in the art.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$c_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The term "optionally substituted" denotes the presence or absence of the substituent group. For example, optionally substituted alkyl includes both unsubstituted alkyl and substituted alkyl. The substituents used to substitute a specified group can be further substituted, typically with one or more of the same or different groups selected from the various groups specified above.

"Carrier" refers to a diluent, adjuvant, excipient or vehicle with which a compound is administered.

The term "amino acid" refers to an organic compound containing an amino group ($NH_2$), a carboxylic acid group (COOH), and any of various side groups. For example, the twenty two amino acids that are naturally incorporated into polypeptides (a.k.a. natural amino acids or naturally occurring amino acids) have the structural formula $NH_2CHRCOOH$, wherein R is a moiety including hydrogen, optionally substituted hydrocarbon moiety, etc. It is commonly known that certain amino acids have two stereoisomers designated as L and D amino acids. Amino acids as mentioned herein include L isomer, D isomer, or a mixture thereof. Furthermore, any of the L, D, or mixed amino acids may further contain additional steroisomeric center(s) in their structures.

The term "peptidyl group", as used herein, denotes an organic moiety derived from one or more amino acid(s) by removal of a hydrogen atom from the $NH_2$ and/or OH group of the amino acid(s). When the peptidyl group is derived from a single amino acid, it is a monopeptidyl group. When the peptidyl group is derived from a molecule of multiple amino acids, it is a multipeptidyl group, e.g., dipeptidyl or tripeptidyl. The amino acids in a multipeptidyl group is linked with each other via amide bond(s).

By "immediate-release" or "instant-release", it is meant a conventional or non-modified release in which greater than or equal to about 75% of the active agent is released within two hours of administration, specifically within one hour of administration.

By "sustained release", it is meant a dosage form in which the release of the active agent is controlled or modified over a period of time. Sustained can mean, for example, extended-, controlled-, delayed-, timed-, or pulsed-release at a particular time. Alternatively, controlled can mean that the release of the active agent is extended for longer than it would be in an immediate-release dosage form, e.g., at least over several hours.

By "effective amount" or "therapeutically effective amount" it is meant the amount of the present compound that, when administered to a patient for treating a disease, such as one related to sialic acid deficiency, is sufficient to effect such treatment for the disease. The "effective amount" or "therapeutically effective amount" will vary depending on the active agent, the disease and its severity, and the age, weight, and other conditions of the patient to be treated.

The terms "treating" and "treatment", as used herein, refer to an approach for obtaining beneficial or desired results including clinical results. For purposes of this invention, beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, increasing production of sialic acid, the sialylation precursor CMP-sialic acid (e.g., increasing intracellular production of sialic acid) and restoring the level of sialylation in muscle and other proteins, decreasing the dose of one or more other medications required to treat the disease, and/or increasing the quality of life. "Treating" a patient with a compound or composition described herein includes management of an individual to inhibit or cause regression of a disease or condition.

"Prophylaxis" or "prophylactic treatment" "or preventive treatment" refers to prevention of the occurrence of symptoms and/or their underlying cause, for example, prevention of a disease or condition in a patient susceptible to developing a disease or condition (e.g., at a higher risk, as a result of genetic predisposition, environmental factors, predisposing diseases or disorders, or the like). Prophylaxis includes HIBM myopathy in which chronic disease changes in the muscles are irreversible and for which animal model data suggests treatment benefit in prophylaxis.

The term "patient" refers to an animal, for example, a mammal and includes, but is not limited to, human, bovine, horse, feline, canine, rodent, or primate. Preferably, the patient is a human.

Embodiments of the Compounds

In one aspect, the present invention is directed to sialic acid analogs which are converted, at least in part, to sialic acid upon administration to a patient.

In one embodiment, the present invention is directed to a compound represented by a structural Formula (I):

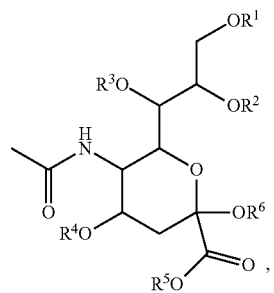

(I)

or a pharmaceutically acceptable salt or solvate thereof; wherein:

$R^2$, $R^3$, $R^4$, and $R^6$ are independently hydrogen or a moiety selected from structural formula (a), (b), (c), (d), (e), (f), and (g):

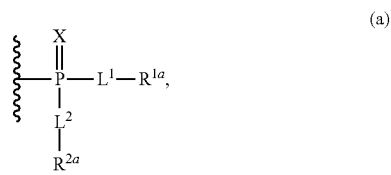

(a)

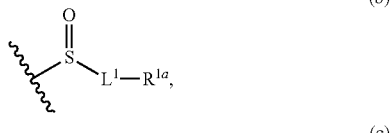

(b)

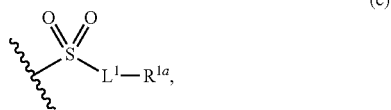

(c)

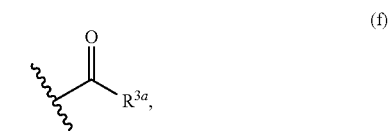

(f)

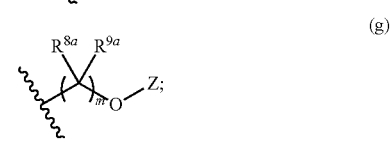

(g)

$R^1$ is a moiety selected from structural formula (a), (b), (c), (d), (e), (f), and (g); or a nucleoside phosphate moiety;

X is oxygen or sulfur;

$L^1$ and $L^2$ are each independently a covalent bond, —O—, or —$NR^{10a}$—;

$R^{10a}$ is hydrogen or optionally substituted alkyl;

$R^{1a}$ and $R^{2a}$ are each independently hydrogen, optionally substituted alkyl, optionally substituted heteroalkyl, optionally substituted aryl, optionally substituted heteroaryl, optionally substituted carbocyclyl, optionally substituted heterocyclyl, —$X^a$—C(O)—O—$R^{11a}$, or —$X^a$—O—C(O)—O—$R^{11a}$, $X^a$ is optionally substituted alkylene;

each $R^{11a}$ is independently hydrogen, optionally substituted alkyl, or optionally substituted heteroalkyl;

$R^{3a}$ is optionally substituted alkyl; or alternatively, $R^{3a}$, together with the carboxyl moiety to which it is attached, form a monopeptidyl or dipeptidyl group;

each $R^{8a}$ and $R^{9a}$ is independently hydrogen or optionally substituted alkyl;

m is 1 or 2;

Z is hydrogen, lower alkyl, an amide group, a lactam group, an ester group, a lactone group, an urea group, a cyclic urea group, a carbonate group, a cyclic carbonate group, a carbamate group, a cyclic carbamate group, or a moiety selected from (a), (b), (c), (d), (e), and (f);

$R^5$ is hydrogen, $G^+$, optionally substituted alkyl, or a moiety selected from (a), (b), (c), (d), (e), (f), and (g); and $G^+$ is a charged organic amine moiety; or alternatively, $OR^3$ and $OR^6$ are taken together to form a lactone structure represented by Formula (Ia):

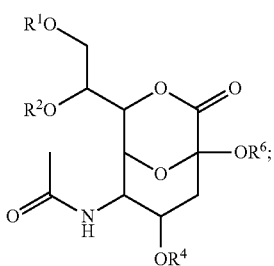

and with the following provisos:

(a) at least one of $R^1$, $R^2$, $R^3$, $R^4$, $R^5$, and $R^6$ is not H; and (b) $R^{3a}$ is not optionally substituted alkyl unless $OR^3$ and $OR^6$ are taken together to form a lactone structure of Formula (Ia) or $R^5$ is (f).

In one embodiment of the present invention, the structural Formula (I) is represented by structural Formula (II), and structural Formula (II) is represented by structural Formula (IIa):

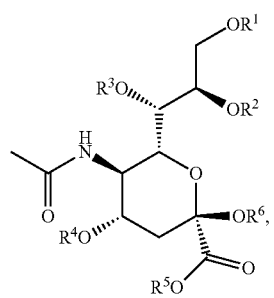

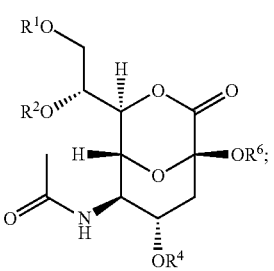

$R^1$, $R^2$, $R^3$, $R^4$, $R^5$, and $R^6$ are the same as previously defined.

In one embodiment of structural Formula (I) or (II), $R^5$ is hydrogen, $Y^+$, optionally substituted alkyl, or structural formula (g).

In one embodiment of structural Formula (I) or (II), at least one of $R^2$, $R^3$, and $R^4$ is hydrogen. In one embodiment of structural Formula (I) or (II), at least two of $R^2$, $R^3$, and $R^4$ are hydrogen. In one embodiment of structural Formula (I) or (II), $R^2$, $R^3$, and $R^4$ are hydrogen.

In one embodiment of structural Formula (I) or (II), $R^6$ is hydrogen.

In one embodiment of structural Formula (I) or (II), m is 1; $R^{8a}$ is hydrogen; and $R^{9a}$ is hydrogen or lower alkyl.

In one embodiment of structural Formula (I) or (II), $R^1$ is selected from structural formula (a), (b), (c), (d), (e), and (f); or a nucleoside phosphate moiety; and $R^2$, $R^3$, $R^4$, $R^5$, and $R^6$ are hydrogen.

In one embodiment of structural Formula (I) or (II), $R^1$ is selected from structural formula (a), (b), (c), (d), (e), and (f); or a nucleoside phosphate moiety; $R^2$, $R^3$, $R^4$, and $R^6$ are hydrogen; and $R^5$ is optionally substituted alkyl or structural formula (g).

In one embodiment of structural Formula (I) or (II), $R^1$ is structural formula (a); and at least one of $L^1$ and $L^2$ is —O—. In one embodiment, $R^5$ is hydrogen or structural formula (g). In another embodiment, Z is hydrogen, lower alkyl, or structural formula (a). In yet another embodiment, wherein $L^1$ and $L^2$ are —O—. In yet another embodiment, $R^{1a}$ and $R^{2a}$ are independently hydrogen, optionally substituted lower alkyl, or optionally substituted aryl. In yet another embodiment, $R^2$, $R^3$, $R^4$, and $R^6$ are hydrogen.

In one embodiment of structural Formula (I) or (II), wherein $R^1$ is structural formula (a); X is oxygen or sulfur; $L^1$ and $L^2$ are —O—; $R^{1a}$ and $R^{2a}$ are independently hydrogen, lower alkyl, or aryl; $R^2$, $R^3$, $R^4$, and $R^6$ are hydrogen; $R^5$ is hydrogen or structural formula (g); and Z is hydrogen, lower alkyl, or structural formula (a).

In one embodiment of structural Formula (I) or (II), $R^1$ is structural formula (b) or (c); and $L^1$ is —O—. In one embodiment, $R^5$ is hydrogen or structural formula (g). In another embodiment, Z is hydrogen, lower alkyl, or structural formula (b) or (c). In yet another embodiment, $R^{1a}$ is hydrogen, optionally substituted lower alkyl, or optionally substituted aryl. In yet another embodiment, $R^2$, $R^3$, $R^4$, and $R^6$ are hydrogen.

In one embodiment of structural Formula (I) or (II), $R^1$ is structural formula (b) or (c); $L^1$ is —O—; $R^{1a}$ is hydrogen, lower alkyl, or aryl; $R^2$, $R^3$, $R^4$, and $R^6$ are hydrogen; $R^5$ is hydrogen or structural formula (g); and Z is hydrogen, lower alkyl, or structural formula (b) or (c).

In one embodiment of structural Formula (I) or (II), $R^1$ is structural formula (f); $R^{3a}$, together with the carboxyl moiety to which it is attached, form a monopeptidyl or dipeptidyl group; and the monopeptidyl or dipeptidyl group is derived from naturally occurring amino acid, non-naturally occurring amino acid, or a combination thereof In one embodiment, the monopeptidyl or dipeptidyl group of $R^{3a}$ is derived from amino acids selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine, and a combination thereof.

In one embodiment of structural formula (f), the monopeptidyl group can be represented by structural fomula (d) and (e):

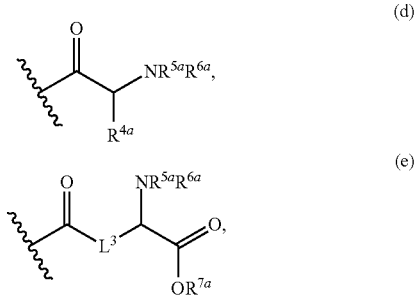

(d)

(e)

$R^{4a}$ is hydrogen, halogen, nitro, cyano, optionally substituted alkyl, optionally substituted alkenyl, optionally substituted aryl, optionally substituted heteroalkyl, optionally substituted heterocyclyl, optionally substituted heteroaryl, optionally substituted carbocyclyl, OR, $NR_2$, or SR; each R, $R^{7a}$, $R^{5a}$, and $R^{6a}$, is independently hydrogen or optionally substituted alkyl; or alternatively, $R^{4a}$ and $NR^{5a}R^{6a}$, together with the carbon atom to which they are attached, or $R^{5a}$ and $R^{6a}$, together with the nitrogen atom to which they are attached, form an optionally substituted four- to seven-membered azacyclic ring which optionally contains one or more additional heteroatom(s) selected from oxygen, nitrogen, and sulfur; and $L^3$ is optionally substituted alkylene.

In one embodiment of structural Formula (I) or (II), $R^1$ is structural formula (d) or (e); $R^{4a}$ is hydrogen, halogen, cyano, optionally substituted alkyl, optionally substituted heteroalkyl, OR, $NR_2$, or SR; R, $R^{7a}$, $R^{5a}$, and $R^{6a}$ is independently hydrogen or lower alkyl; $L^3$ is optionally substituted C1 to C6 alkylene; and the optional substituent is selected from the group consisting of halogen, nitro, cyano, hydroxyl, alkoxy, amino, N-alkyl amino, N, N-dialkylamino, =O, acyl, carboxyl, carboxyl ester, amide, optionally substituted aryl, optionally substituted heterocyclyl, optionally substituted heteroaryl, and optionally substituted carbocyclyl. In one embodiment, $R^5$ is hydrogen or structural formula (g). In another embodiment, Z is hydrogen, lower alkyl, or structural formula (d) or (e). In yet another embodiment, $R^2$, $R^3$, $R^4$, and $R^6$ are hydrogen.

In one embodiment of structural formula (f), the dipeptidyl group can be represented by structural Formula (h) or (i):

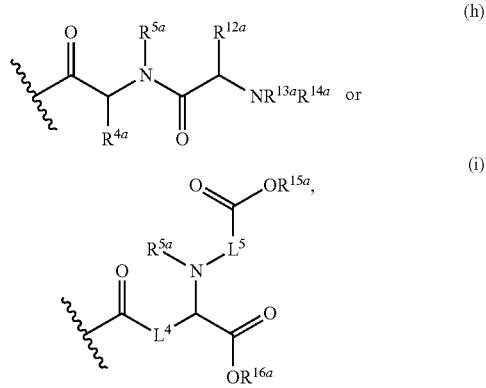

(h)

(i)

wherein, $R^{4a}$ and $R^{5a}$ are the same as previously defined; $R^{12a}$ is hydrogen, halogen, nitro, cyano, optionally substituted alkyl, optionally substituted alkenyl, optionally substituted aryl, optionally substituted heteroalkyl, optionally substituted heterocyclyl, optionally substituted heteroaryl, optionally substituted carbocyclyl, =O, OR, $NR_2$, or SR; $R^{13a}$ and $R^{14a}$, are independently hydrogen or optionally substituted alkyl; or alternatively, $R^{12a}$ and $NR^{13a}R^{14a}$, together with the carbon atom to which they are attached, or $R^{13a}$ and $R^{14a}$, together with the nitrogen atom to which they are attached, form an optionally substituted four- to seven-membered azacyclic ring which optionally contains one or more additional heteroatom(s) selected from oxygen, nitrogen, and sulfur; $R^{15a}$ and $R^{16a}$ are independently hydrogen or optionally substituted alkyl; and $L^4$ and $L^5$ are independently optionally substituted alkylene. In one embodiment, $R^5$ is hydrogen or structural formula (g). In another embodiment, Z is hydrogen, lower alkyl, or structural formula (f). In yet another embodiment, $R^2$, $R^3$, $R^4$, and $R^6$ are hydrogen.

In one embodiment of structural Formula (I) or (II), $R^1$, $R^2$, $R^3$, $R^4$, and $R^6$ are hydrogen; and $R^5$ is $G^+$. In one embodiment, G is selected from the group consisting of choline, diolamine, diethylamine, t-butyl amine, and ethanolamine.

In one embodiment of structural Formula (I) or (II), $R^1$, $R^2$, $R^3$, $R^4$, and $R^6$ are hydrogen; and $R^5$ is optionally substituted alkyl or structural formula (g). In one embodiment, $R^5$ is lower alkyl or structural formula (g); m is 1; $R^{8a}$ is hydrogen; $R^{9a}$ is hydrogen or lower alkyl; and Z is an amide group, a lactam group, an ester group, a lactone group, an urea group, a cyclic urea group, a carbonate group, a cyclic carbonate group, a carbamate group, or a cyclic carbamate group.

In one embodiment of structural Formula (I) or (II), $R^1$ is a nucleoside phosphate moiety; and $R^2$, $R^3$, $R^4$, $R^5$, and $R^6$ are hydrogen. In one embodiment, the nucleoside phosphate moiety is an adenosine monophosphate (AMP) moiety or an adenosine triphosphate (ATP) moiety.

In one embodiment, the present invention provides a compound of Formula (III):

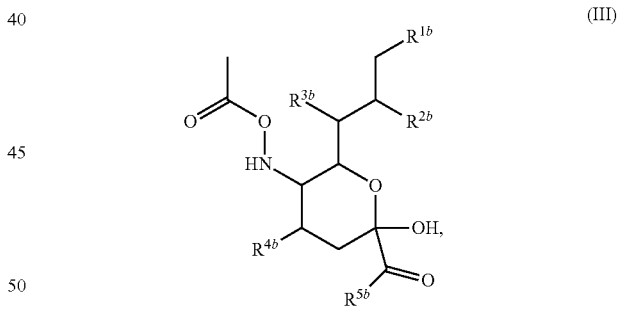

(III)

or a pharmaceutically acceptable salt or solvate thereof; wherein:

$R^{1b}$, $R^{2b}$, $R^{3b}$, $R^{4b}$, and $R^{5b}$ are independently OH, —O—C(O)—Y, or —O—(CHR)$_n$—O—C(O)—Y; with the proviso that at least one of $R^{1b}$, $R^{2b}$, $R^{3b}$, and $R^{4b}$ and $R^{5b}$ is not OH;

n is 1 or 2;

$R^b$ is hydrogen or lower alkyl;

each —O—C(O)—Y is independently a peptidyl moiety; and the presence of one or more —O—C(O)—Y in Formula (III) increases the uptake of the compound thereof by peptide transporter 1 (PepT1) as compared to the uptake of a compound of Formula (III) wherein $R^{1b}$, $R^{2b}$, $R^{3b}$, $R^{4b}$, and $R^{5b}$ are OH.

In one embodiment, structural Formula (III) is represented by structural Formula (IV):

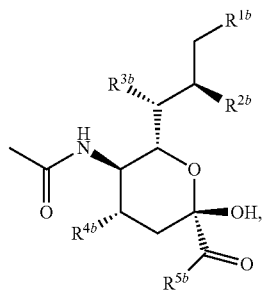

(IV)

$R^{1b}$, $R^{2b}$, $R^{3b}$, $R^{4b}$, and $R^{5b}$ are the same as previously defined.

In one embodiment of structural Formula (III) or (IV), $R^{2b}$, $R^{3b}$, and $R^{4b}$ are OH.

In one embodiment of structural Formula (III) or (IV), $R^{1b}$ is —O—C(O)—Y and $R^{5b}$ is OH.

In one embodiment of structural Formula (III) or (IV), $R^{1b}$ is —O—C(O)—Y; and $R^{5b}$ is —O—(CHR)$_n$—O—C(O)—Y.

In one embodiment of structural Formula (III) or (IV), the peptidyl moiety of is a monopeptidyl moiety derived from an amino acid selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine. In aother embodiment, the monopeptidyl moiety is derived from an amino acid selected from the group consisting of Aspartic acid, Lysine, Proline, and Valine.

In one embodiment of structural Formula (III) or (IV), the peptidyl moiety is a dipeptidyl moiety derived from any of two amino acids selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine, and a combination thereof. In aother embodiment, the dipeptidyl moiety is derived from (1) Aspartic acid and Alanine, or (2) glutamic acid and Alanine.

In one embodiment of structural Formula (III) or (IV), n is 1; and $R^b$ is hydrogen.

In one embodiment of structural Formula (I), the compound is represented by structural Formula (Ia):

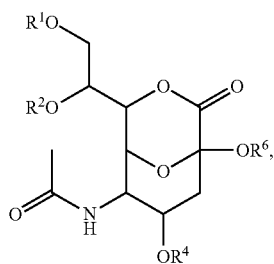

(Ia)

wherein $R^1$, $R^2$, and $R^4$ are hydrogen; and $R^6$ is structural formula (d), (e), or (f).

In one embodiment of structural Formula (Ia), $R^6$ is structural formula (f); and $R^{3a}$ is C1 to C12 alkyl.

In one embodiment of structural Formula (Ia), wherein $R^6$ is structural formula (f); and $R^{3a}$, together with the carboxyl moiety to which it is attached, form a monopeptidyl or dipeptidyl group.

In one embodiment of structural Formula (Ia), the monopeptidyl or dipeptidyl group is derived from naturally occurring amino acid, non-naturally occurring amino acid, or a combination thereof.

In one embodiment of the present invention, structural Formula (I) is represented by structural Formula (V):

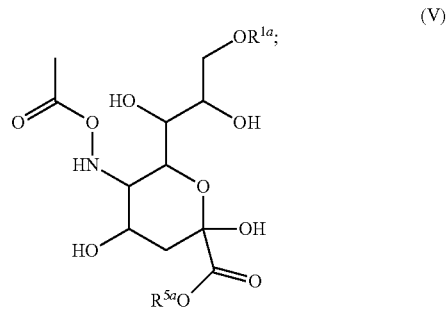

(V)

wherein $R^{1a}$ is structural (f), and $R^{3a}$, together with the carboxyl moiety to which it is attached, form a monopeptidyl or dipeptidyl group; and $R^{5a}$ is structural (f), and $R^{3a}$ is optionally substituted alkyl.

In one embodiment of structural Formula (V), $R^{3a}$, together with the carboxyl moiety to which it is attached, form a monopeptidyl group which is derived from amino acids selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine. In one embodiment, the monopeptidyl group is derived from amino acids selected from the group consisting of Aspartic acid, Lysine, Proline, and Valine.

In one embodiment of structural Formula (V), $R^{3a}$, together with the carboxyl moiety to which it is attached, form a dipeptidyl group which is derived from any two amino acids selected from the group consisting of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine, and a combination thereof. In one embodiment, the dipeptidyl group is derived from two amino acids selected from (1) Aspartic acid and Alanine, or (2) glutamic acid and Alanine.

In one embodiment of structural Formula (V), $R^{1a}$ is structural (f), and $R^{3a}$ is unsubstituted C1 to C6 alkyl.

In one embodiment of structural Formula (V), $R^{1a}$ is structural (f), and $R^{3a}$ is C1 to C6 alkyl substituted with one or more groups selected from alkoxy, hydroxyl, amino, N-alkyl amino, N-dialkyl amino, halo, nitro, cyano, —C(O)—R', —C(O)—NH2, —C(O)—NHR', —C(O)—NR'R', —C(O)—OH, —C(O)—OR'; or two substituents, together with the atoms to which they are attached, form an optionally substituted carbocyclyl or heterocyclyl containing one or more heteroatom(s) selected from nitrogen, oxygen, and sulfur; wherein each R' is independently an optionally substituted alkyl.

In some specific embodiments, the compounds of the present invention are selected from the group consisting of
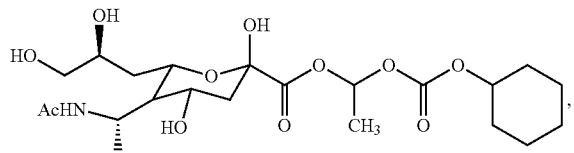
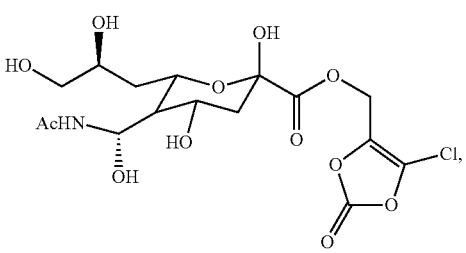
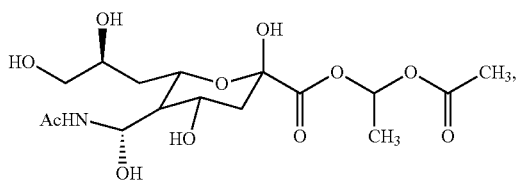
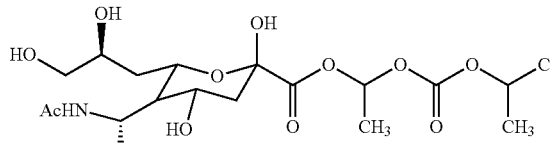
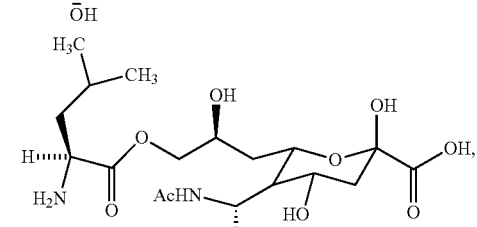
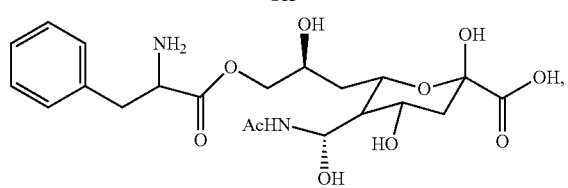
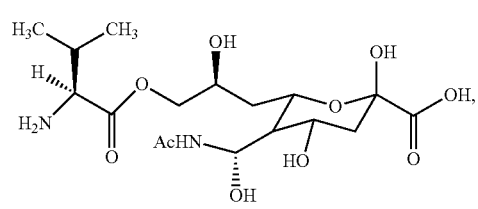
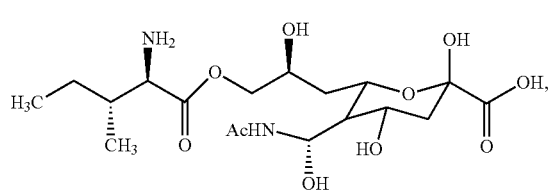
-continued
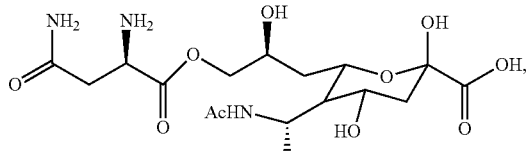
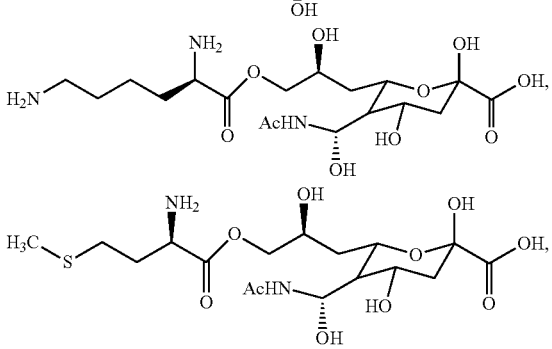
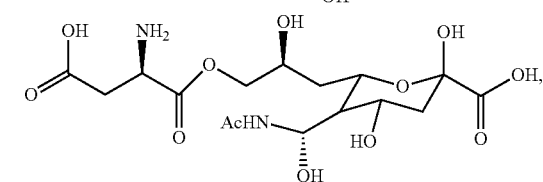
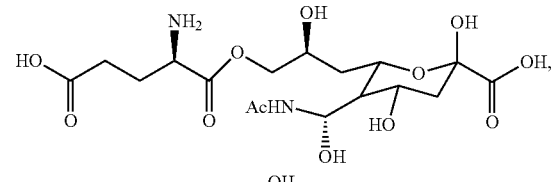
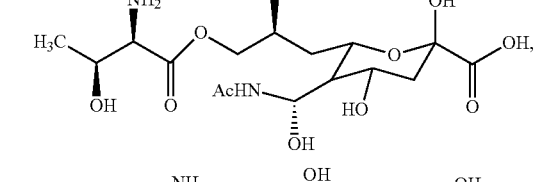
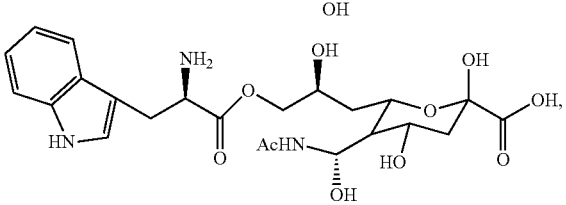
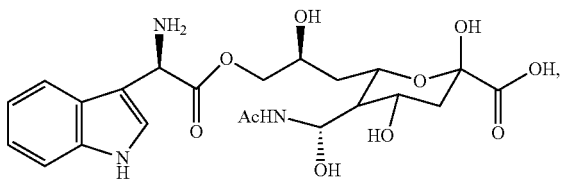

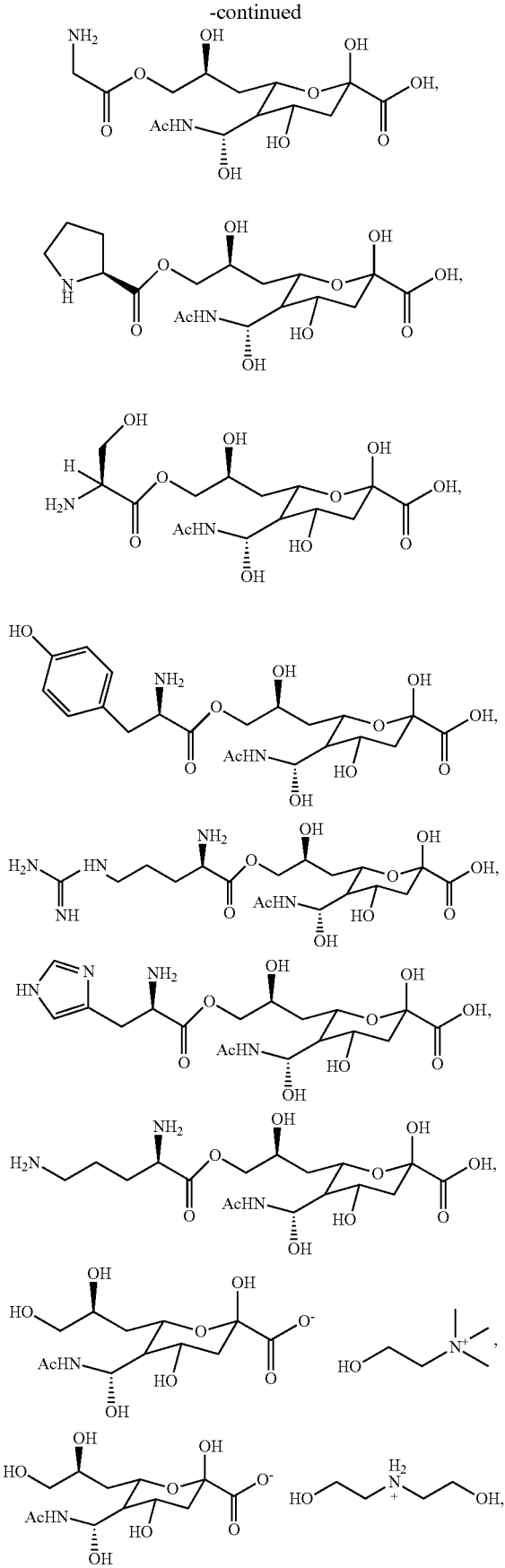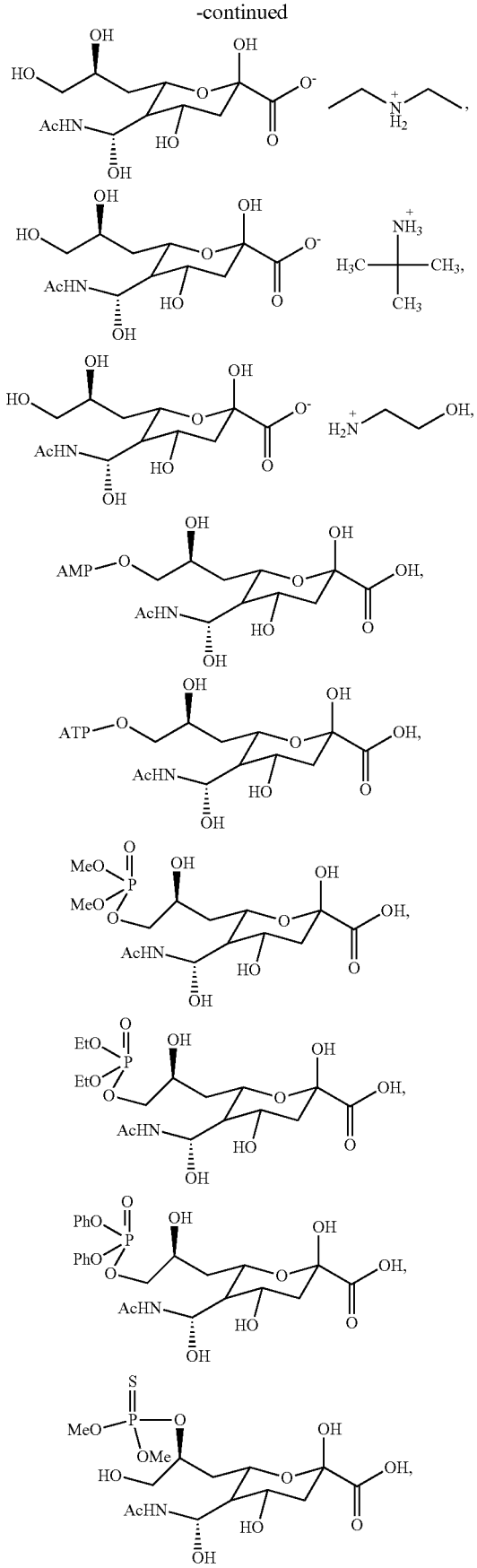

25
-continued
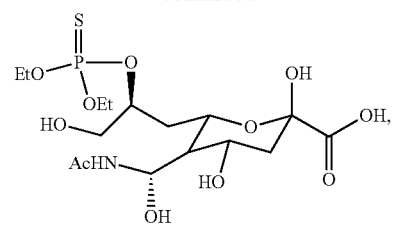
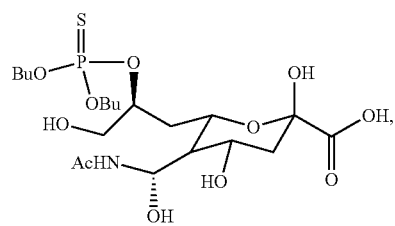
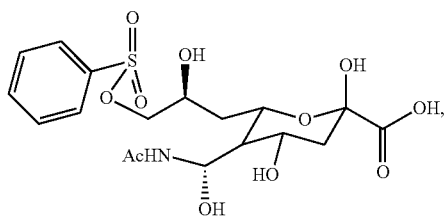
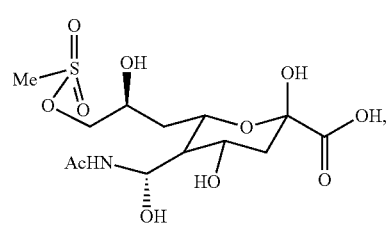
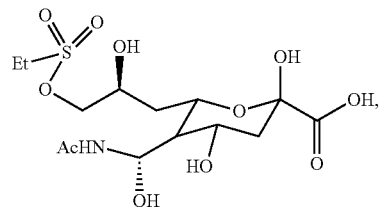
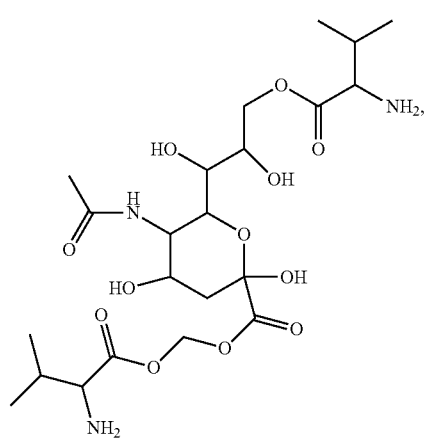
26
-continued
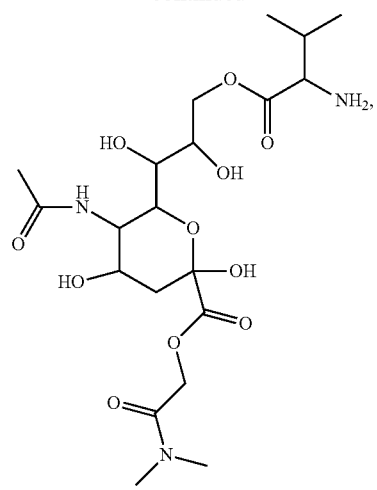
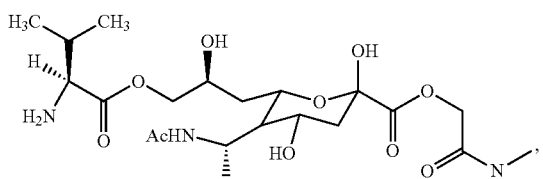
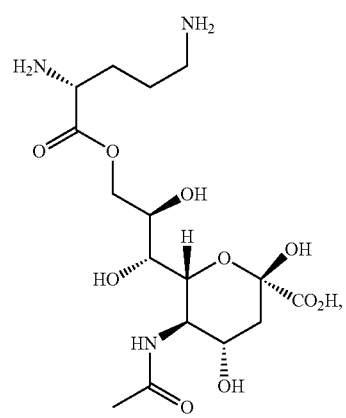
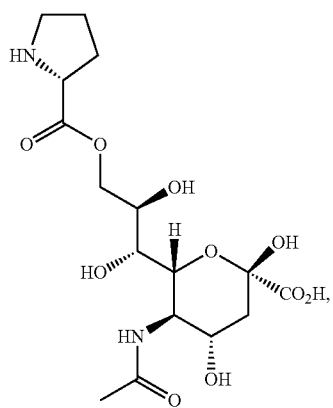

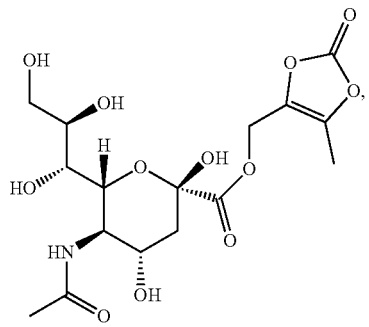

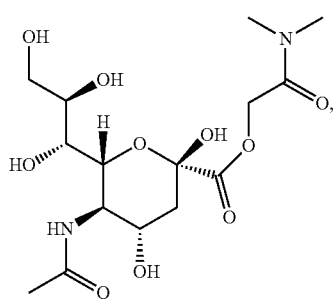

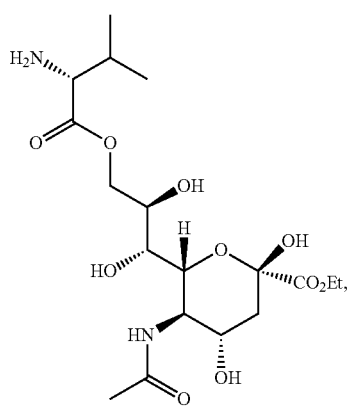

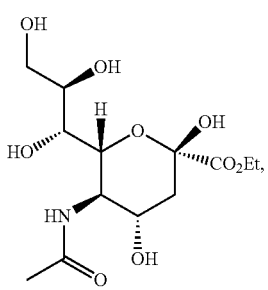

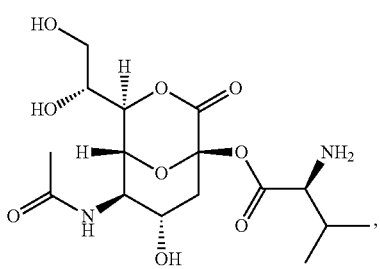

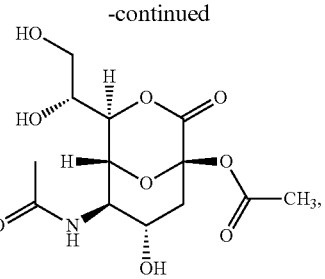

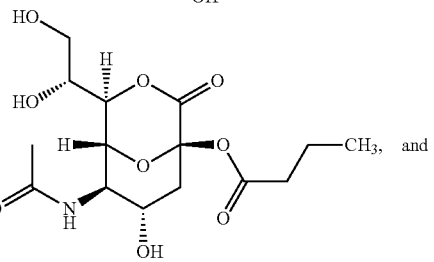

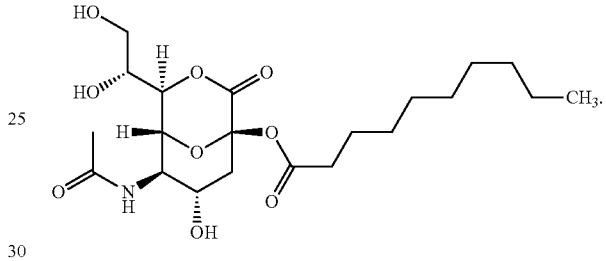

Embodiments of the Utilities of the Present Compounds

In one embodiment of the present invention, the present compounds can be used for the treatment of sialic acid deficiencies by administering an effective amount of the present compound, or a pharmaceutically acceptable salt or solvate thereof, to a patient in need of such treatment. In another embodiment, the method comprises administering a present compound, or a pharmaceutically acceptable salt or solvate thereof, to a patient in need of such treatment; wherein upon administration, the compound, or a pharmaceutically acceptable salt or solvate thereof, continuously provides a therapeutically effective amount of sialic acid for more than about 4 hours.

In one embodiment, the sialic acid deficiency is a myopathy associated with sialic acid deficiency. In one embodiment, the myopathy associated with sialic acid deficiency is Hereditary Inclusion Body Myopathy (HIBM), Nonaka myopathy, and/or Distal Myopathy with Rimmed Vacuoles (DMRV).

In other embodiments, the method can continuously provide a therapeutically effective amount of sialic acid for a period from about 1 hour to about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours.

In one embodiment, the therapeutically effective amount refers to the amount administered to the patient. In another embodiment, the therapeutically effective amount refers to the amount delivered to the bloodstream of the individual. In yet another embodiment, the therapeutically effective amount refers to the amount delivered to muscle tissue of the individual. The present compounds, upon administration, are converted to sialic acid in vivo. That is, the present compounds, upon administration, are metabolized to one or more compounds in the sialic acid pathway or derivatives thereof (including sialic acid itself).

In one embodiment, the present method can deliver to the blood stream of a patient one or more compounds in the sialic acid pathway or derivatives thereof (including sialic acid itself) with a $C_{max}$ of about 0.2 to about 40 µg/mL or about 2 to about 40 µg/mL. In another embodiment, the therapeutically effective amount denotes one or more compounds in the sialic acid pathway or derivatives thereof (including sialic acid itself) with a $C_{max}$ of about 5 to about 40 µg/mL.

In one embodiment, the present method can deliver to the blood stream of a patient one or more compounds in the sialic acid pathway or derivatives thereof (including sialic acid itself) with a trough level of about 0.1 to about 20 µg/mL. In other embodiments, the present method can deliver to a patient in need of the treatment one or more compounds in the sialic acid pathway or derivatives thereof (including sialic acid itself) with a trough level of about any one of 0.1-15 µg/mL, 0.1-10 µg/mL, 0.1-5 µg/mL, 0.5-20 µg/mL, 0.5-15 µg/mL, 0.5-10 µg/mL, 0.5-5 µg/mL, 1-20 µg/mL, 1-15 µg/mL, 1-10 µg/mL, or 1-5 µg/mL or about any one of 0.1, 0.5, 1 1.5, 2, 2.5, 3, 3.5, 4, 4.5, 5, 5.5, 6, 7, 8, 9, 10, 11, 12, 13, 14 or 15 µg/mL.

In one embodiment, a patient is administered about any of 0.1 to 40 g/day, 0.2 to 20 g/day, 0.5 to 10 g/day, 0.5 to 5 g/day, or 0.5 to 4 g/day of one or more of the present compound. In one embodiment, a patient is administered about any of 0.2 g/day to 5 g/day, 0.3 g/day to 4 g/day, or 0.5 g/day to 3 g/day of one or more of the present compounds.

In other embodiments, a patient is administered about any of 0.01-500 mg/kg, 0.05-300 mg/kg, 0.1-150 mg/kg, 0.5-100 mg/kg, or 1-50 mg/kg of one or more compounds of the present invention. In some embodiments, the present method is capable of delivering to a patient in need thereof from about any of 1 mg/kg and 40 mg/kg, 1.5 mg/kg and 35 mg/kg, or 2 mg/kg and 30 mg/kg of one or more compounds in the sialic acid pathway or derivatives thereof (including sialic acid itself).

Embodiments of Compositions and Routes of Administration

A compound of the present invention can be formulated as a pharmaceutical composition. In one embodiment, such a composition comprises a present compound, or a pharmaceutically acceptable salt or solvate thereof, and a pharmaceutically acceptable carrier. The pharmaceutical composition can then be administered orally, parenterally, by inhalation spray, rectally, or topically in dosage unit formulations containing conventional nontoxic pharmaceutically acceptable carriers, adjuvants, and vehicles as desired. The amount of active ingredient that can be combined with the carrier materials to produce a single dosage form varies depending upon the mammalian host treated and the particular mode of administration. Topical administration can also involve the use of transdermal administration such, as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., REMINGTON'S PHARMACEUTICAL SCIENCES, Mack Publishing Co., Easton, Pa.; 1975. Other examples of drug formulations can be found in Liberman, H. A. and Lachman, L., Eds., PHARMACEUTICAL DOSAGE FORMS, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a compound of the invention can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A compound of the invention can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The dosage regimen utilizing the compounds of the present invention in combination with an anticancer agent is selected in accordance with a variety of factors including type, species, age, weight, sex and medical condition of the patient; the severity of the condition to be treated; the route of administration; the renal and hepatic function of the patient; and the particular compound or salt or ester thereof employed. A consideration of these factors is well within the purview of the ordinarily skilled clinician for the purpose of determining the therapeutically effective dosage amounts to be given to a person in need of the instant combination therapy.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

Dosage levels are dependent on the nature of the condition, drug efficacy, the condition of the patient, the judgment of the practitioner, and the frequency and mode of administration; optimization of such parameters is within the ordinary level of skill in the art.

In one embodiment, the present invention provides a sustained release pharmaceutical composition comprising a compound of the present invention, or a pharmaceutically acceptable salt or solvate thereof, wherein the release of the compound is over a period of about 4 hours or more. In other embodiments, the release of the compound is over a period of about 5, about 6, about 7, about 8, about 9, about 10, about 11, about 12, about 13, about 14, about 15, about 16, about 17, about 18, about 19, about 20, about 21, about 22, about 23, or about 24 hours.

In another embodiment, the present invention provides a sustained release pharmaceutical composition comprising a compound of the present invention, or a pharmaceutically acceptable salt or solvate thereof, wherein the pharmacological effect from the compound lasts about 4 hours or more upon administration of the composition. In other embodiments, the pharmacological effect from the compound lasts about 5, about 6, about 7, about 8, about 9, about 10, about 11, about 12, about 13, about 14, about 15, about 16, about 17, about 18, about 19, about 20, about 21, about 22, about 23, or about 24 hours.

In another embodiment, the present invention provides a sustained release pharmaceutical composition comprising a compound of the present invention, or a pharmaceutically acceptable salt or solvate thereof; wherein the composition, upon administration, provides a therapeutically effective amount of the compound for about 4 hours or more. In other embodiments, the composition provides a therapeutically effective amount of the compound for about 5, about 6, about 7, about 8, about 9, about 10, about 11, about 12, about 13, about 14, about 15, about 16, about 17, about 18, about 19, about 20, about 21, about 22, about 23, or about 24 hours.

In one embodiment of any of the above-described sustained release pharmaceutical composition, the composition contains a matrix which comprises a compound of the present invention, or a pharmaceutically acceptable salt or solvate thereof; and one or more release rate controlling polymers. In one embodiment, the matrix is in form of a core or a layer over a core.

In one embodiment, the matrix comprises one or more polymers selected from the group consisting of a) at least one water-swellable, pH independent polymer, b) at least one anionic, pH-dependent, gel-forming copolymer, c) at least one cationic polymer, and d) at least one hydrocolloid polymer.

In one embodiment of any of the above-described sustained release pharmaceutical composition, the composition contains a release rate controlling membrane disposed over: a pull layer comprising a compound of the present invention, or a pharmaceutically acceptable salt or solvate thereof, and an osmotic push layer; wherein the release rate controlling membrane has an orifice immediately adjacent to the pull layer. In one embodiment, the pull layer further comprises a release rate controlling polymer.

In one embodiment of any of the above-described sustained release pharmaceutical composition, the composition comprise one or more particles, and each of the particles comprises an active core comprising a compound of the present invention, or a pharmaceutically acceptable salt or solvate thereof; and a release rate controlling polymer disposed over the core.

In one embodiment of any of the above-described sustained release pharmaceutical composition, the composition comprises one or more particles, and each of the particles comprises an inert core, an active layer comprising a compound of the present invention, or a pharmaceutically acceptable salt or solvate thereof disposed over the inert core, and a release rate controlling polymer disposed over the active layer.

Various sustained release systems for drugs have also been devised, and can be applied to compounds of the invention. See, for example, U.S. Pat. No. 5,624,677, International Patent Application No. PCT/US2011/043910, and U.S. patent application Ser. No. 12/595,027; the disclosures of which are incorporated herein by reference in their entireties for all purposes.

PREPARATION AND EXAMPLES

Standard procedures and chemical transformation and related methods are well known to one skilled in the art, and such methods and procedures have been described, for example, in standard references such as Fiesers' Reagents for Organic Synthesis, John Wiley and Sons, New York, NY, 2002; Organic Reactions, vols. 1-83, John Wiley and Sons, New York, NY, 2006; March J. and Smith M., Advanced Organic Chemistry, 6th ed., John Wiley and Sons, New York, NY; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

Synthesis of the examples of presented compounds is illustrated in the following schemes and procedures. The general synthetic schemes and related procedures used for the preparation of the examples compounds are given hereinafter.

Scheme 1. Synthetic Route for Monoester Prodrug 1.

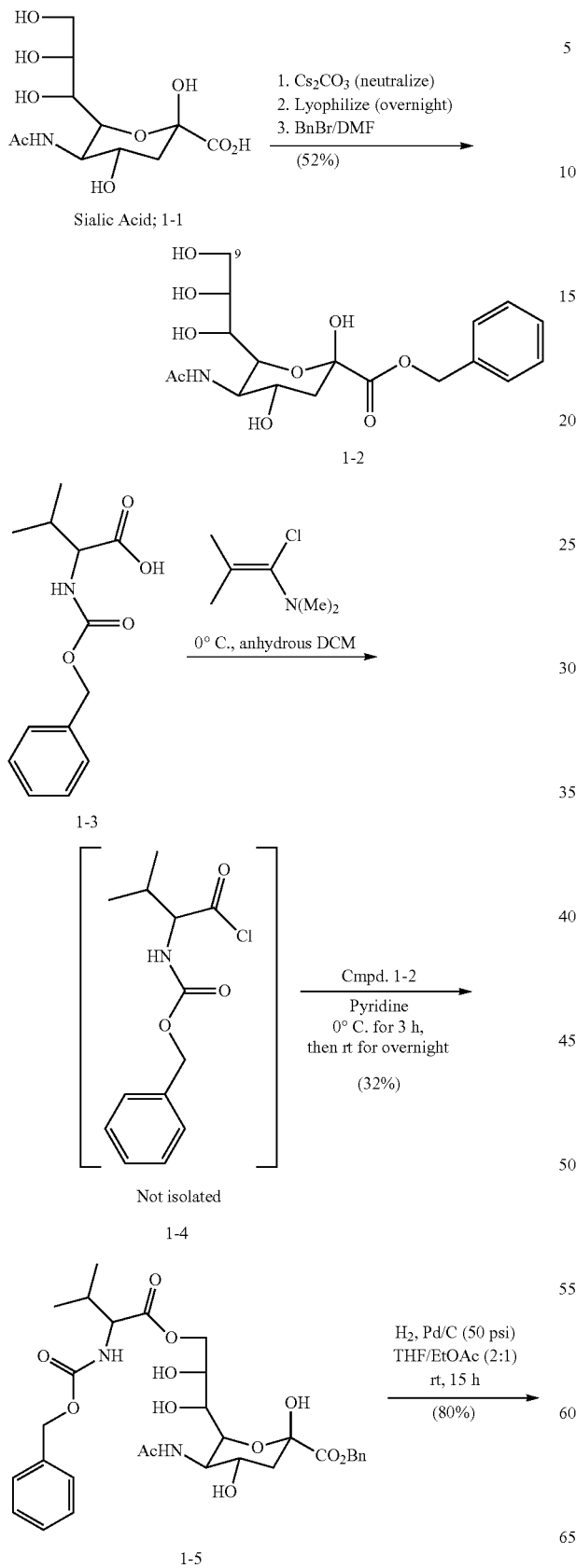

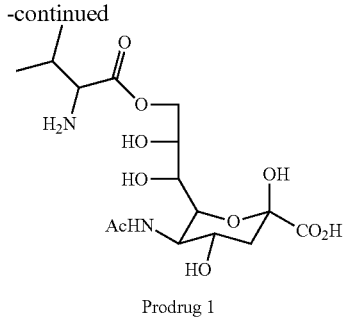

Prodrug 1

Example 1

Preparation of N-Acetyl-B-neuraminic Acid Benzyl ester-(1-2).

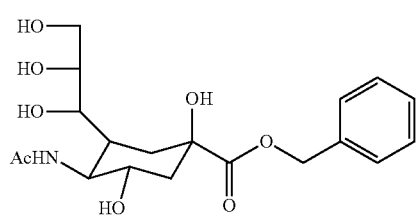

1-2

| S. No. | Chemicals/Reagents & Solvents | MW | mmol | Eq. | Amt |
|---|---|---|---|---|---|
| 1 | Sialic Acid (1-1) | 309.37 | 64.7 | 1.0 | 20.0 g |
| 2 | HPLC grade water | | | | 100 mL |
| 3 | 10% aqueous Cs$_2$CO$_3$ | | | | Added until neutral pH. |
| 4 | Benzyl Bromide (d = 1.44 g/ml) | 171.04 | 350 | 5.4 | 42 mL |
| 5 | Dimethylformamide (DMF) | | | | 160 mL |

In a 500 mL lyophilization vessel, Sialic acid (20.0 g, 64.7 mmol) is dissolved in HPLC grade water (100 mL). At room temperature, the resulting acidic solution is then neutralized to approximately pH 7.0 (litmus paper) by the addition of a 10% aqueous solution of Cesium Carbonate. The resulting clear solution is frozen and placed on a Lyophilizer for 1-2 days until a flakey dry white powder is obtained. The powder is then dissolved in anhydrous DMF (160 mL) and placed under an atmosphere of argon gas to give a light suspension (mostly soluble). To this is then added Benzyl Bromide (dropwise via syringe) at room temperature under an argon balloon, at which time the solution becomes clear. The solution is stirred overnight at room temperature leading to the formation of a white suspension of cesium bromide. The white solid (not desired product) is filtered through a Celite pad and the pad washed with copious amounts of DMF. The DMF is then removed under high vacuum with the temperature bath not exceeding 50° C. to give a viscous, pale yellow syrup. In order to remove excess benzyl bromide, the syrupy residue is triturated using a mixture of diethyl ether and hexanes (approx 2:1) and the solvent is decanted off. The remaining syrup is then dissolved is a minimum of isopropanol and placed in the freezer for several hours. A precipitate forms at this time which is filtered through a Buchner funnel and collected to provide 10.95 g of pure N-Acetyl-β-neuraminic Acid Benzyl ester as a white solid. Diethyl ether is added in small amounts to the mother liquor to induce crystallization of a second lot of product benzyl ester (625 mg.). Total Yield=10.95 (Crop 1)+625 mg. (crop 2)=11.58 g (52% yield). LC/MS: (+) ESI: m/z=400.1 [M+1]; 422.1 [M+Na, major signal]; retention time=2.53 min. $^1$H NMR (400 MHz, d$^4$-MeOD) δ 7.31-7.46 (m, 5H), 5.25 (dd, J=22.0, 12.8 Hz), 3.92-4.11 (m, 2H), 3.77-3.89 (m, 2H), 3.70-3.76 (m, 2H), 3.65 (dd, J=16.0, 8.0 Hz, 1H), 3.52 (dd, J=9.2, 1.2 Hz, 1H), 2.26 (dd, J=13.2, 5.2 Hz, 1H), 2.03 (s, 3H), 1.93 (dd, J=12.4, 11.2 Hz, 1H).

Example 2

Preparation of 5-Acetylamino-6-[3-(2-benzyloxy-carbonylamino-3-methyl-butyryloxy)-1,2-dihydroxy-propyl]-2,4-dihydroxy-tetrahydro-pyran-2-carboxylic acid benzyl ester (1-5).

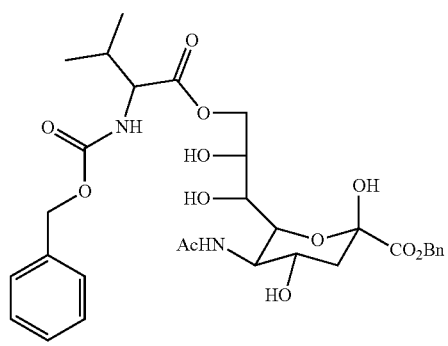

1-5

| S. No. | Chemicals/Reagents & Solvents | MW | mmol | Eq. | Amt |
|---|---|---|---|---|---|
| 1 | N-Acetyl-β-neuraminic Acid Benzyl ester (1-2) | 399.39 | 4.88 | 1.0 | 1.95 g |
| 2 | Carbobenzyloxy-L-Valine | 251.28 | 5.37 | 1.1 | 1.35 g |
| 3 | 1-Chloro-N,N,2-trimethyl-1-propenylamine (Ghosez' Reagent) (d = 1.01) | 133.6 | 6.34 | 1.3 | 847 mg. (848 µL) |
| 4 | Dichloromethane (anhydrous) | | | | 12.0 mL |
| 5 | Pyridine (anhydrous) | | | | 8.0 mL |

To a solution of Carbobenzyloxy-L-Valine (1.35 g, 5.37 mmol) in anhydrous dichloromethane (12 mL) at 0° C. under argon is added 1-Chloro-N,N,-2-trimethyl-1-propenylamine (848 µL, 6.34 mmol) by dropwise addition via a syringe. The resulting solution is then stirred at 0° C. for 10 minutes resulting in a clear colorless solution. To this solution is then added the N-Acetyl-β-neuraminic Acid Benzyl ester (1-2), previously dissolved in anhydrous pyridine (8.0 mL) via dropwise addition. The solution immediately turns yellow and is kept at 0° C. and under an argon atmosphere for 3 hours. The cooling bath is then removed and the solution kept at rt for overnight resulting in a cloudy suspension. The solvents are removed under high vacuum being careful that the temperature bath does not exceed 50° C. to give a light yellow oil. In order to remove traces of pyridine, the oil is triturated with toluene and again evaporated under high vacuum. The remaining oil is dissolved in minimum amount of dichloromethane (DCM) and loaded directly unto a silica gel column (Silicycle-FLH-R10030B-ISO80, 80 g Cartridge) and purified by flash chromatography (Mobile Phase: DCM/Methanol=96/4 to 88/12 over 24 minutes). Combination of the purest fractions yields 996 mg (32% yield) of pure (1-5) as a white solid. LC/MS: (+) ESI: m/z=633.2 [M+1]; 655.2 [M+Na, major signal]; retention time=3.69 min. $^1$H NMR (400 MHz, d$^4$-MeOD) δ 7.12-7.37 (m, 11H), 5.08-5.17 (m, 2H), 4.95-5.03 (m, 2H), 4.28 (dd, J=11.6, 2.0 Hz, 1H, C-9), 4.18 (dd, J=11.6, 6.0 Hz, 1H, C-9'), 4.05-4.06 (m, 1H), 3.91-3.98 (m, 1H), 3.89 (dd, J=10.5, 1.2 Hz, 1H), 3.80-3.86 (m, 11H), 3.70 (t, 1H), 3.41-3.43 (m, 1H), 2.14 (dd, J=12.8, 4.8 Hz, 1H), 1.98-2.08 (m, 1H), 1.91 (s, 3H), 1.79-1.89 (m, 1H), 0.80-0.84 (m, 6H); $^{13}$C NMR (400 mHz, d$^4$-MeOD)δ 173.7, 170.9, 158.9, 136.2, 137.1, 129.6, 129.5, 129.4, 129.1, 129.0, 128.8, 96.7, 72.0, 70.3, 69.3, 68.3, 68.0, 67.8, 61.1, 54.4, 40.7, 32.1, 22.7, 19.6, 18.4.

Example 3

Preparation of 5-Acetylamino-6-[3-(2-amino-3-methyl-butyryloxy)-1,2-dihydroxy-propyl]-2,4-dihydroxy-tetrahydro-pyran-2-carboxylic acid (1).

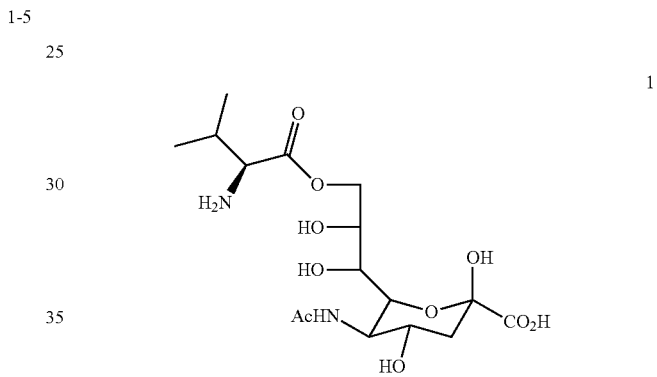

1

| S. No. | Chemicals/Reagents & Solvents | MW | mmol | Eq. | Amt |
|---|---|---|---|---|---|
| 1 | Benzyl Ester (1-5) | 632.6 | 3.96 | 1.0 | 2.50 g |
| 2 | 10% Palladium on Carbon | | | | 2.0 g |
| 3 | Hydrogen (50 psi) overnight | | | | |
| 4 | Tetrahydrofuran | | | | 22 mL |
| 5 | Ethyl Acetate | | | | 10 mL |

In a 500 mL Parr shaker is placed the Z-valine protected benzyl ester (1-5) (2.50 g, 3.96 mmol) and the solid is dissolved in a mixture of THF (22 mL) and ethyl acetate (10 mL). To this is then added 10% Palladium on Carbon (2.0 g) in a single lot and the resulting suspension is hydrogenated at 50 psi at room temperature for overnight. LC/MS at this time of a small filtered aliquot, shows complete absence of starting material and the presence of the desired material (M+1=409). The remaining suspension is filtered through a Celite pad and the pad washed with THF. Evaporation of solvent leaves a light yellow semi-solid which upon trituration with isopropanol produces an off-white solid. The solid is collected by filtration through a Buchner funnel to provide 1.28 g (80% yield) of essentially pure pro-drug ester 1. LC/MS: (+) ESI: m/z=409.0 [M+1]; retention time=0.40 min. Melting Point: Decomposes between 140 to 145° C. Appearance: Off-white solid. Analytical HPLC; Column=Phenomenex Luna HILIC (reverse phase): Mobile Phase: A=0.05% H$_3$PO$_4$ in Water, B=0.05% H$_3$PO$_4$ in CH$_3$CN: Gradient: 5% A to 50% B over 20 minutes, λ=205 nM; Retention Time: 3.8 minutes (Single Peak). $^1$H NMR (400 MHz, d$^4$-MeOD) δ 4.41-4.49 (m, 2H), 3.98-4.08 (m, 3H), 3.87-3.97 (m, 2H), 3.57 (dd, J=9.6, 0.8 Hz, 1H), 2.28-2.39 (m, 1H), 2.22 (dd, J=12.8, 4.8 Hz, 1H), 2.04 (s, 3H), 1.83 (dd, J=12.8, 11.6 Hz, 1H), 1.04-1.06 (m, 6H); $^{13}$C NMR (400 mHz, D2O) δ 176.6, 174.6, 169.9, 96.4, 69.9, 68.4, 67.8, 67.4, 67.2, 58.4, 52.3, 39.4, 29.4, 22.1, 17.3, 17.1. Final Purity Estimate: 96-97% (Based upon $^1$H NMR integration in Trifluoroacetic Acid-D).

Example 4

Sialic acid/Prodrug Single Dose PO Crossover Pharmacokinetics Study in Cynomolgus Monkeys

| Test System | Young adult (2.5-5 yo), Cynomolgus Macaques |
|---|---|
| Drug Status | Non-naive |
| # of Animals | 3 animals (0♂, 3♀) |
| Acclimation | 14 days |
| Dosing Regimen | PO on days 1 and 8 |

| Day | Test Article | Dose Level | Dose Route | No of Animals |
|---|---|---|---|---|
| 1 | Sialic acid | 100 mg/kg | PO | 3 |
| 8 | Prodrug 1 | 100 mg/kg | PO | |

| Test Substance | Sialic Acid and Compound 1 |
|---|---|
| Clinical Observations | Once daily |
| Body Weight | Once weekly |
| Blood Collection for PK | PO arm: Pre-dose −1 and 0, 15, 30 minutes, 1, 2, 4, 8 and 24 hrs. |
| Urine Collection for PK | Pre-dose overnight, 0-4 hrs, 4-8 hrs, 8-12 hrs, 12-24 hrs. Total volumes were determined and 5 ml samples were preserved for possible future analysis. |
| Blank plasma/urine | Blank monkey plasma and urine (up to 100 ml if possible) |
| Quality Assurance | The study will be conducted according to the principles of GLP. |

A single oral dose crossover pharmacokinetic study of sialic acid (API) and prodrug (Compound 1—a valine ester of sialic acid as described above) was run in fasted cynomolgus monkeys (n=3). For this study, it was essential that the GI tract of the in vivo model have some similarities to human metabolism in order for the Pep T1 transporter system to be present, thus monkeys were chosen since they carry the same transporter in the gut as humans.

Figure 2A:
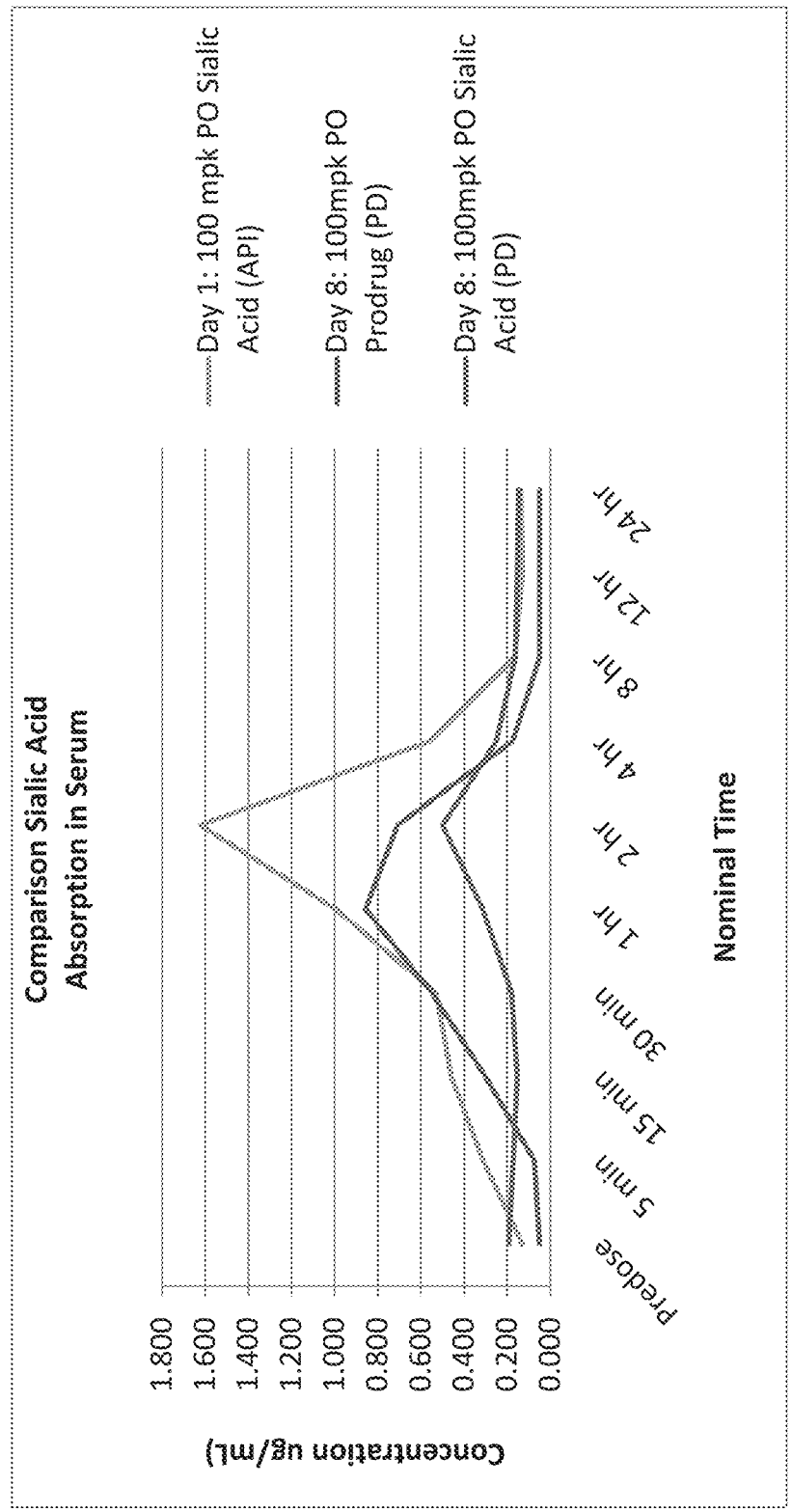
FIGS. 2A-2C are graphs demonstrating the data from a single dose PO crossover pharmacokinetics study of sialic acid and Compound 1 in cynomolgus monkeys.
Figure 2B:
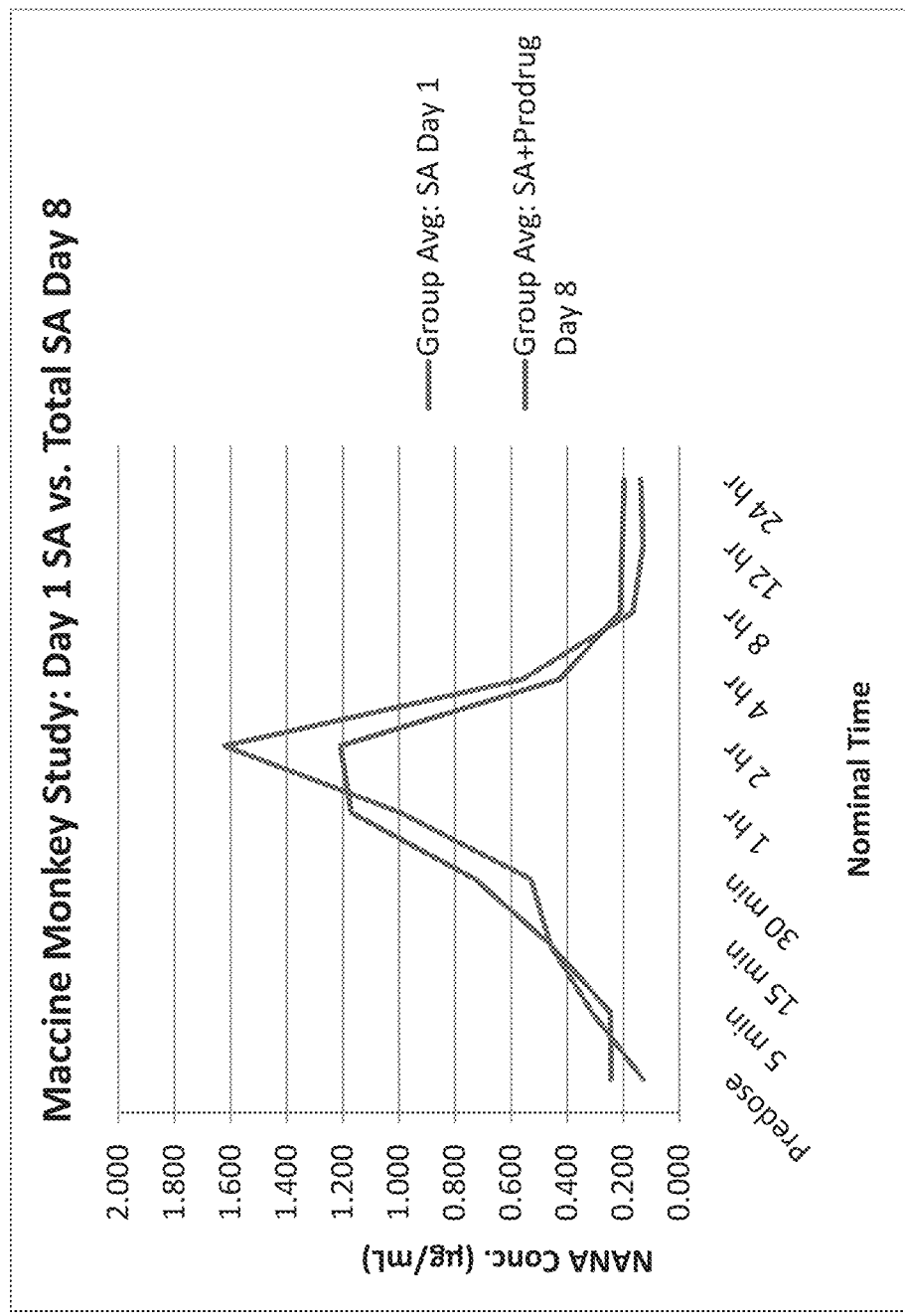
Figure 2C:
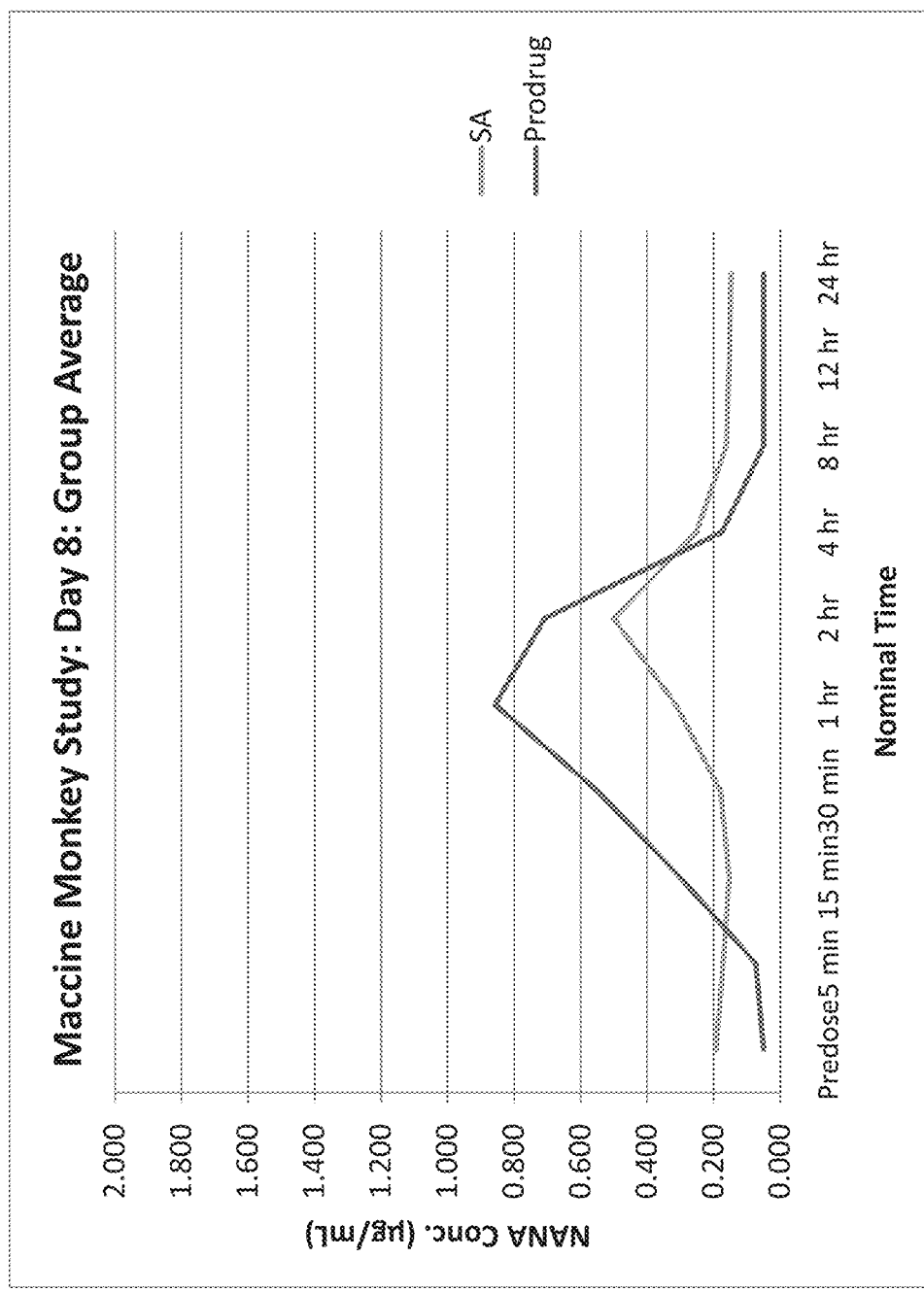
Figure 3A:
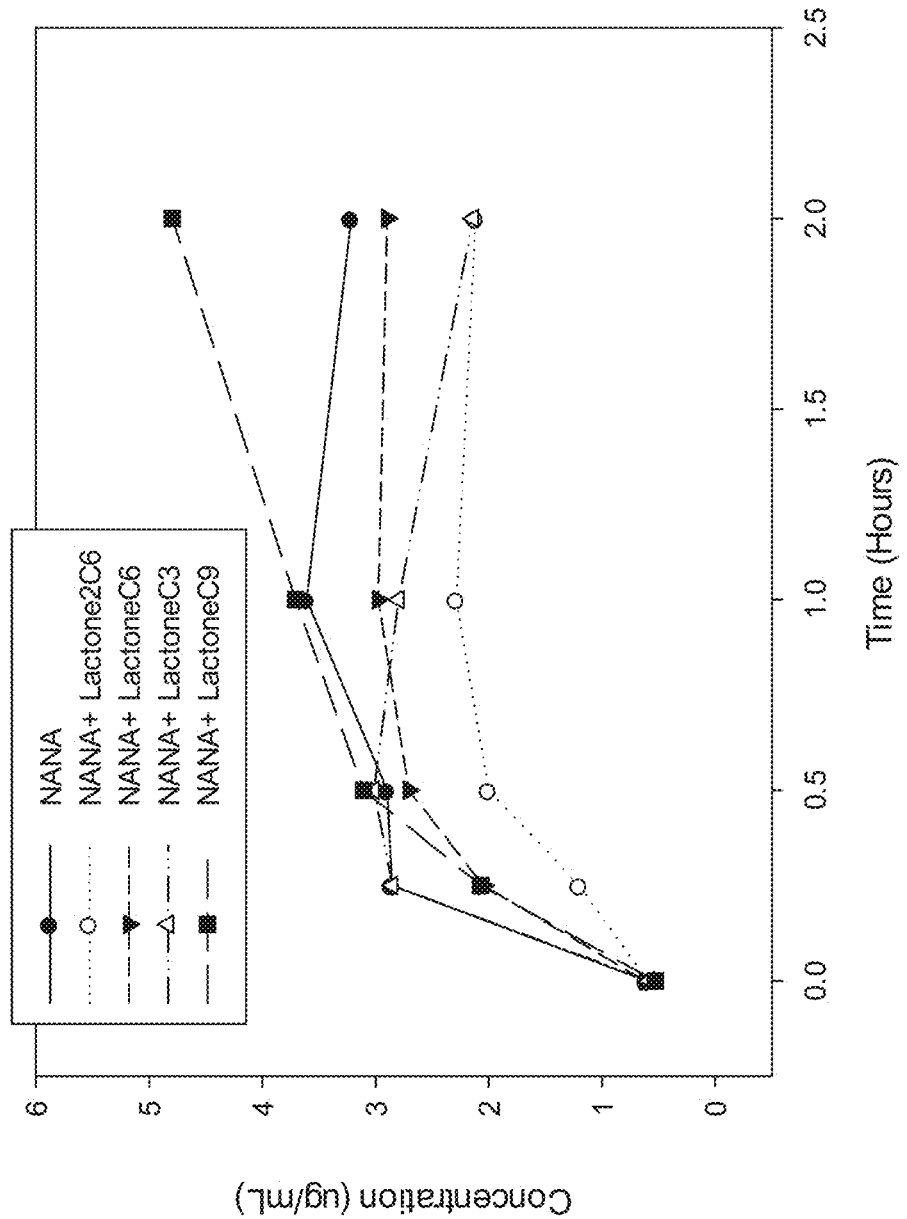
FIGS. 3A-3D show pharmacokinetic data obtained following single dose oral administration of various compounds of the present invention to male Sprague Dawley rats.
Figure 3B:
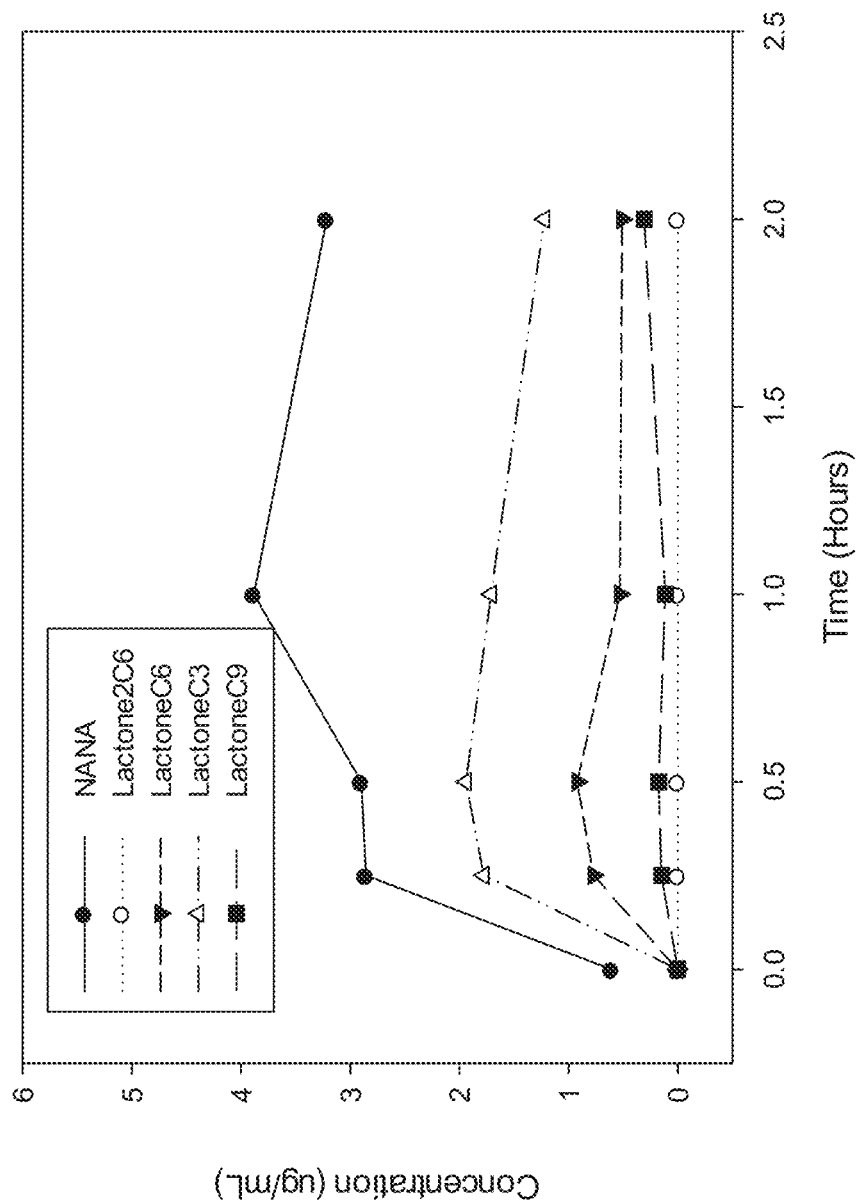
Figure 3C:
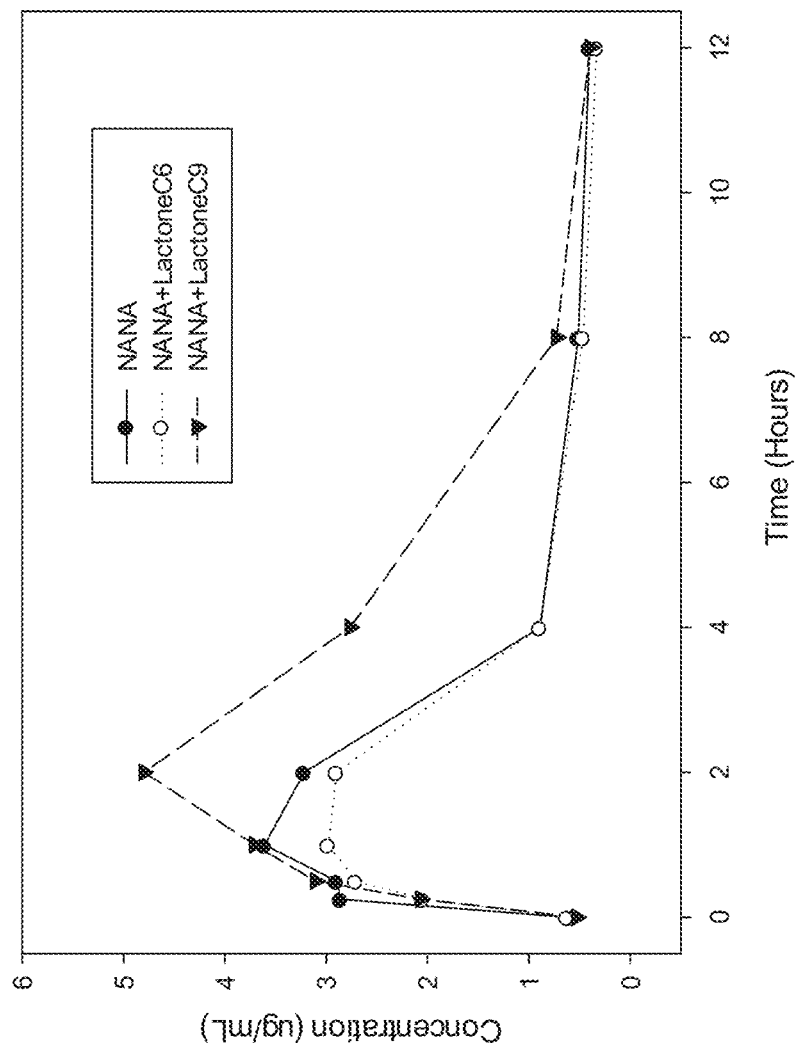
Figure 3D:
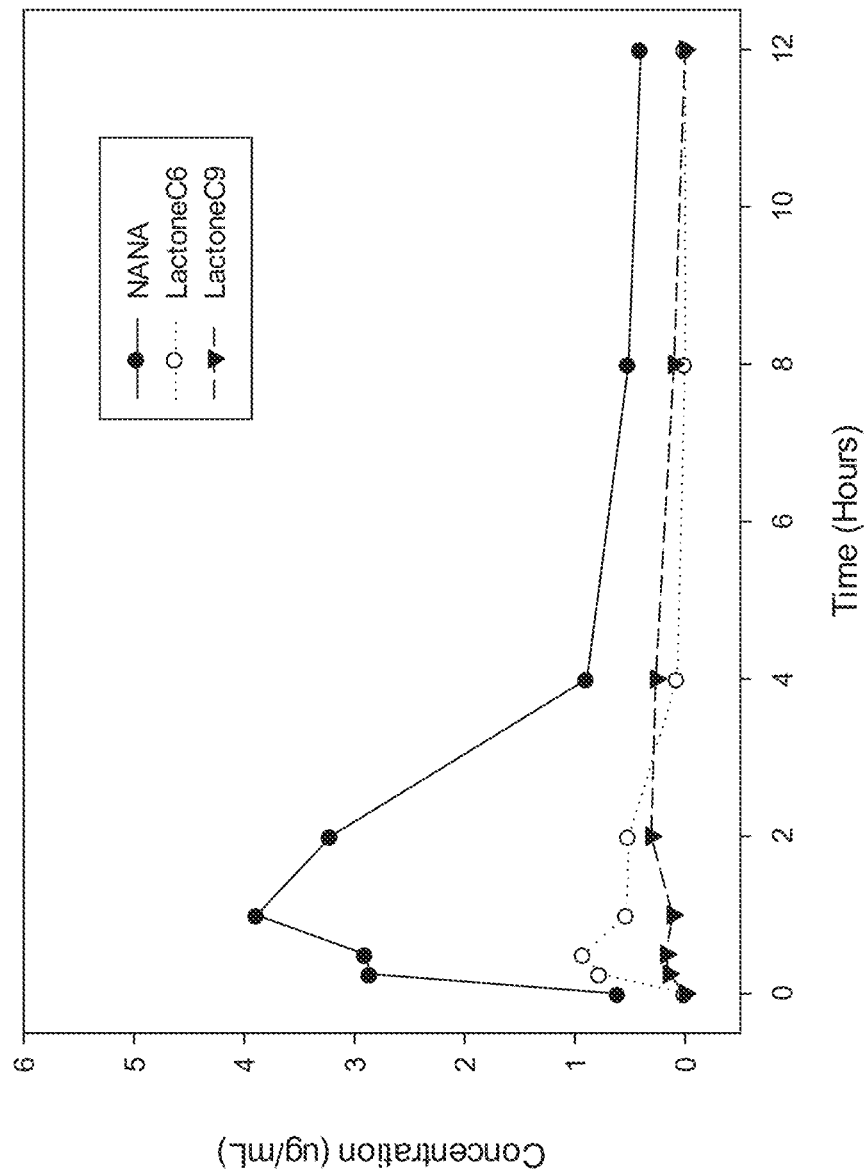
Figure 4A:
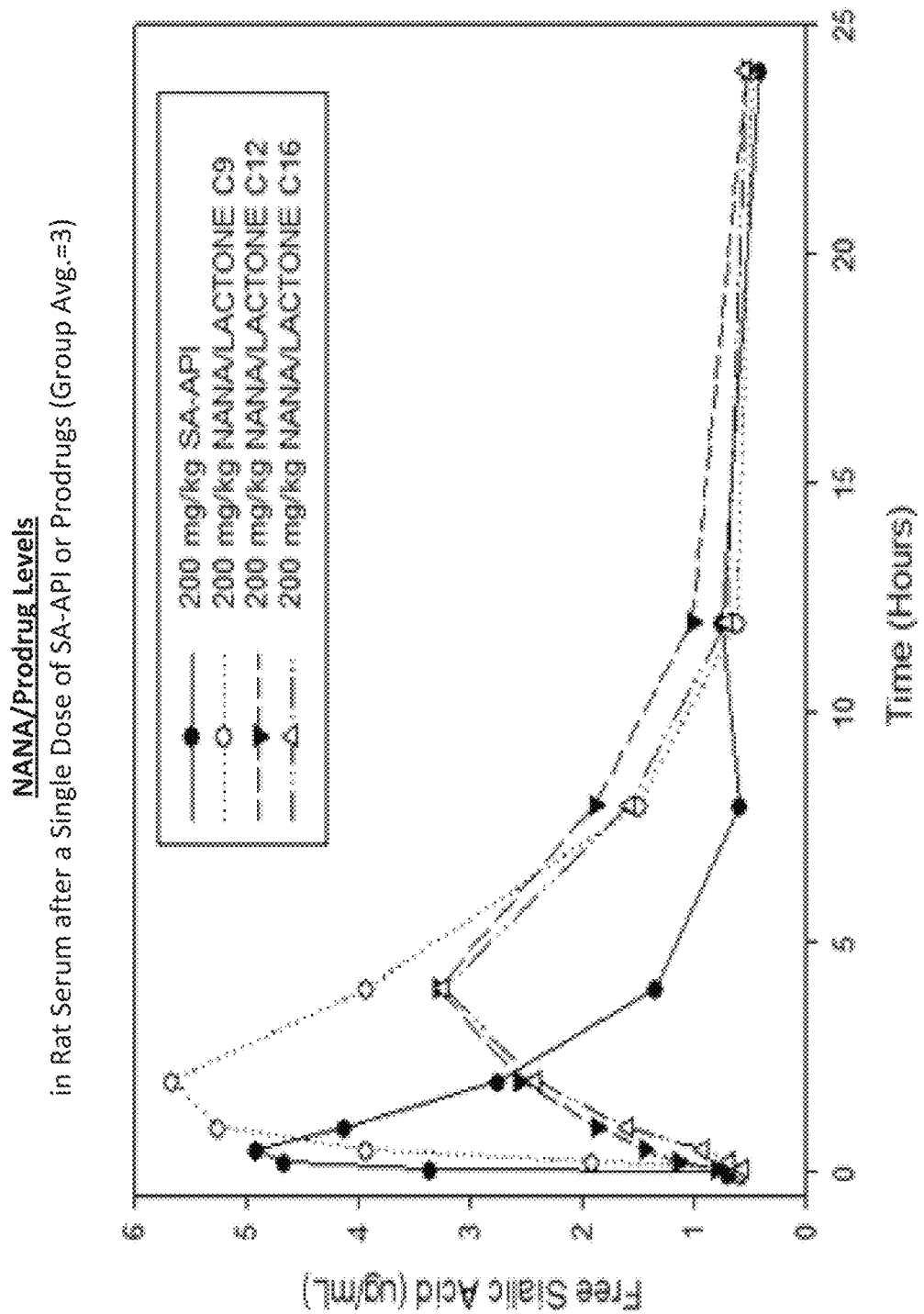
FIG. 4A-4D show pharmacokinetic data obtained following single dose oral administration of various compounds of the present invention to male Sprague Dawley rats.
Figure 4B:
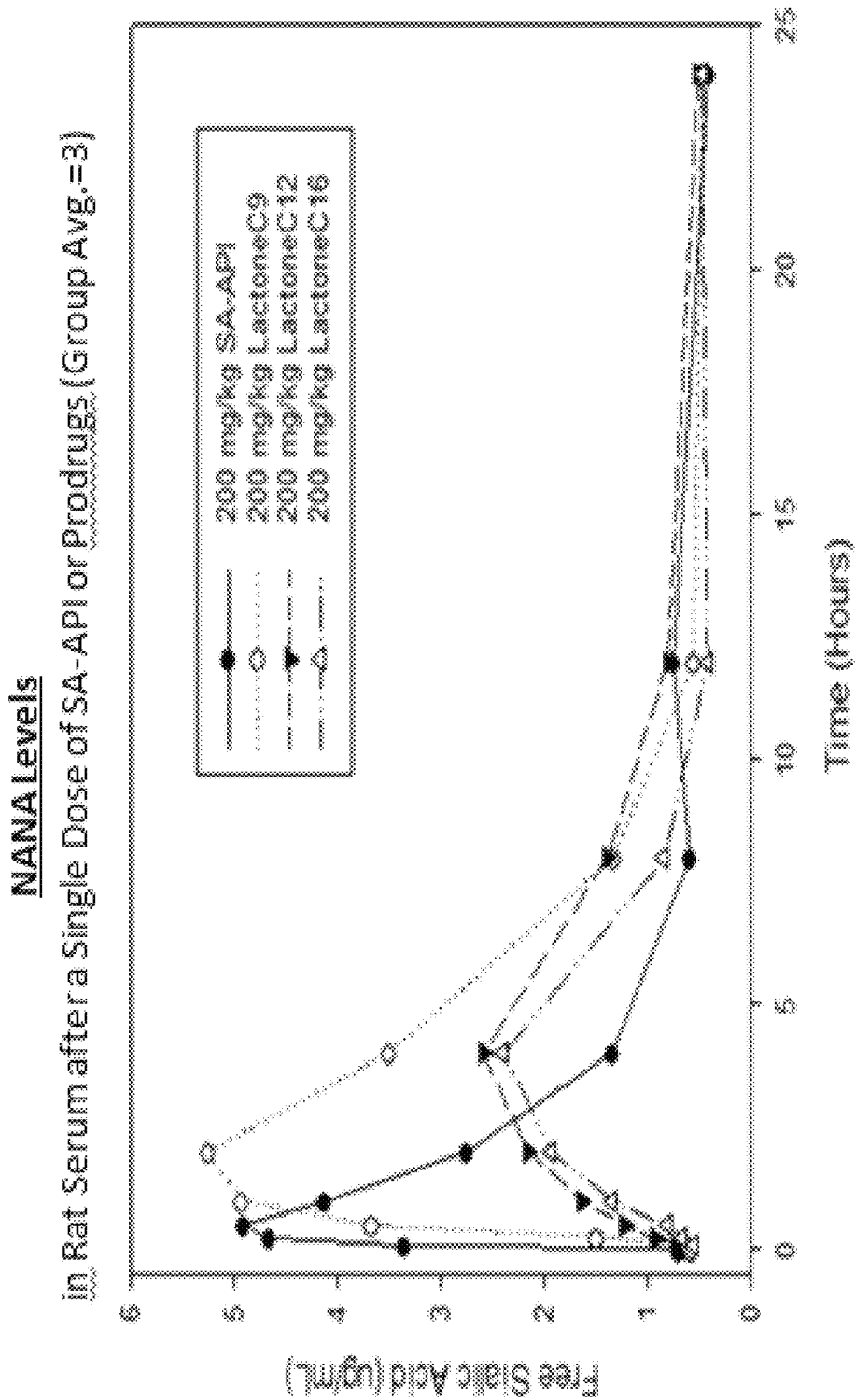
Figure 4C:
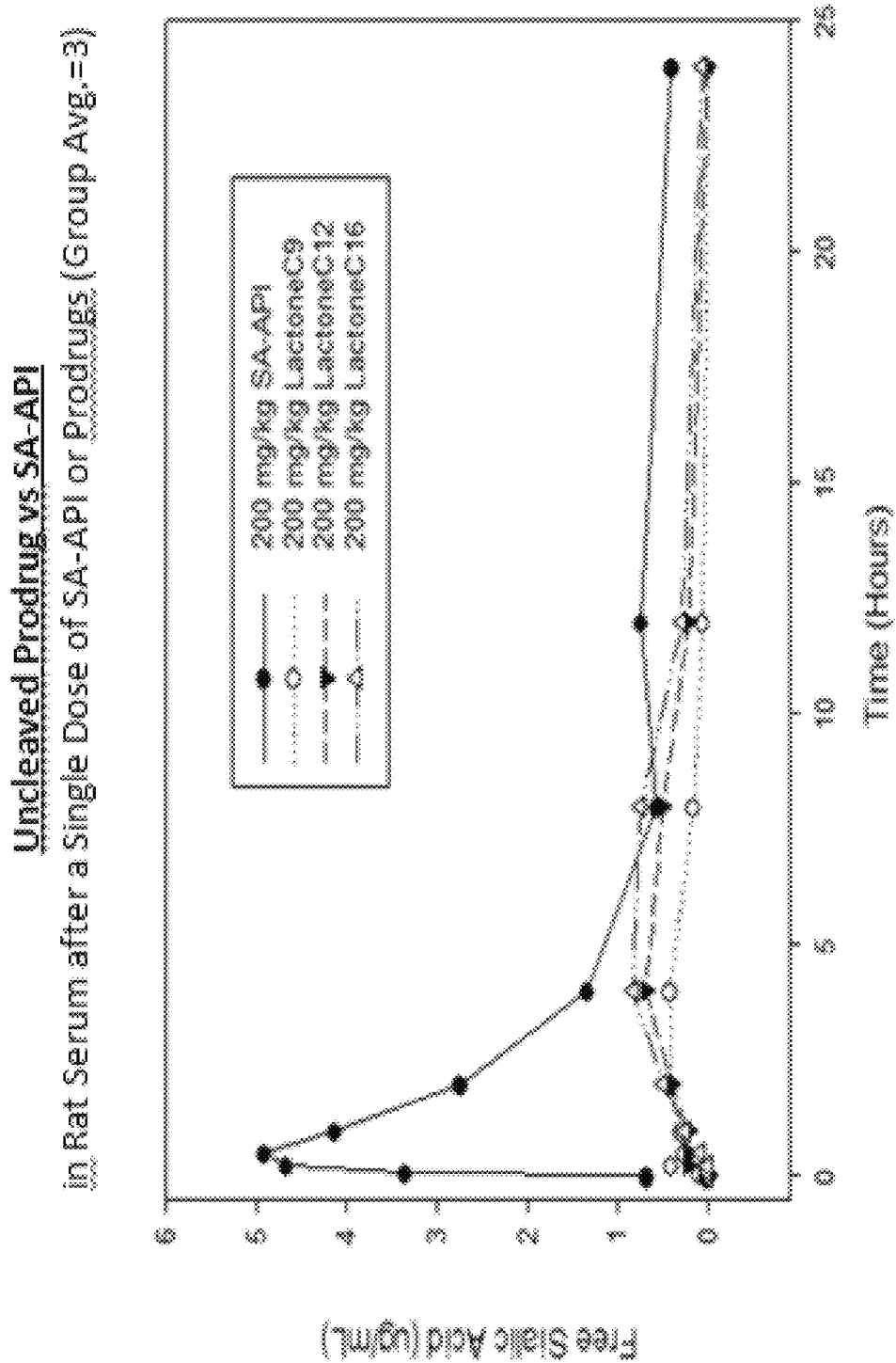
Figure 4D:
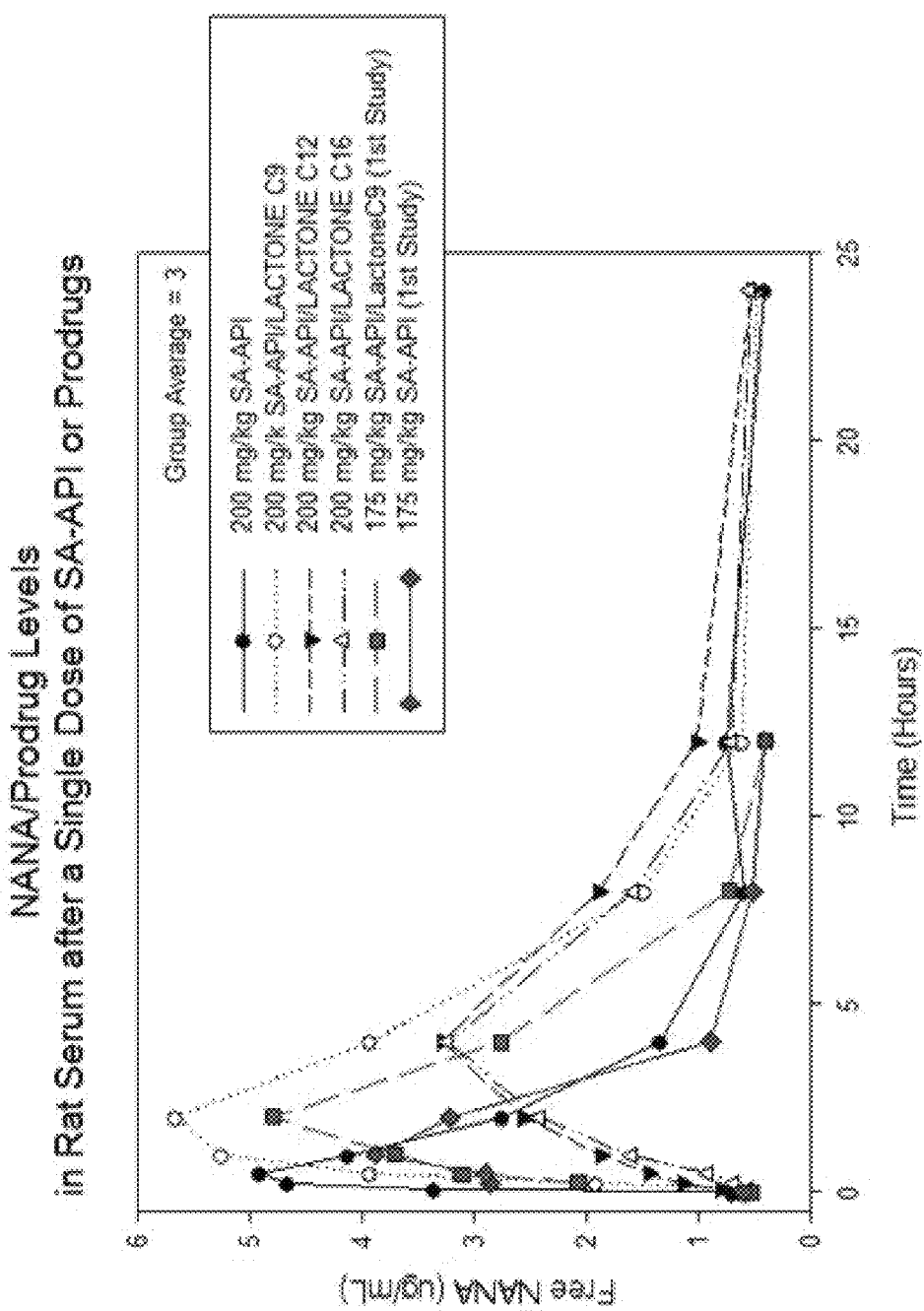

The 100 mg/kg dose level chosen was based on what is known for dosing of sialic acid which has passed complete toxicological evaluation and is safe up to 2,000 mg/kg NOAEL in dogs and rats. On Day 1, three female cynomolgus monkeys were dosed with 100 mg/kg sialic acid (API) and on Day 8 the same three cynomolgus monkeys were dosed with 100 mg/kg of the prodrug. Serum was collected at the following timepoints: predose, then 5 min, 15 min, 30 min, 1 hr, 2 hrs, 4 hrs, 8 hrs, 12 hrs and 24 hrs postdose. Urine samples were collected predose overnight, then at intervals 0-4 hrs, 4-8 hrs, 8-12 hrs and 12-24 hrs post dose. The data in FIG. 2A show the mean absorption values (n=3) of serum sialic acid on Days 1 and 8. The prodrug peak serum concentration is earlier (1 hr) than sialic acid API (2 hrs). While the T$_{max}$ (1.623 µg/mL) for sialic acid API is higher than the prodrug (T$_{max}$=0.857 µg/mL), the extent of the absorption for both drugs are similar. The pharmacokinetic data in FIGS. 2B and 2C show group averages of sialic acid concentrations on Days 1 and 8.

Example 5

Single Dose Pharmacokinetic Studies of Sialic Acid vs. Prodrugs in the Male Sprague Dawley Rat The objective of this study was to investigate the pharmacokinetic profile of Sialic Acid and Prodrugs (Lactone 2C6, Lactone C6, Lactone C3 and Lactone C9) following a single oral administration in the male Sprague Dawley rat. The structures of the Prodrugs are as follows:

Lactone 2C6: (1R,4R,5R,6R,7S)-6-acetomido-4[(R)-2-(hexanoyloxy)-1-hydroxyethyl]-7-hydroxy-2-oxo-3, 9-dioxabicyclo[3.3.1]nonan-1-yl hexanoate:

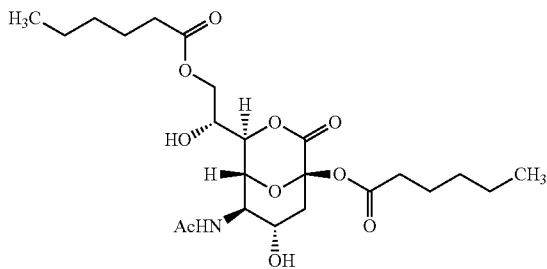 [SMILES: CCCCCC(=O)OC[C@@H](O)[C@H]1OC(=O)[C@]2(OC(=O)CCCCC)C[C@H](O)[C@@H](NC(C)=O)[C@H]1O2]

Lactone C6: (1R,4R,5R,6R,7S)-6-acetomido-4[(R)-1,2-dihydroxyethyl]-7-hydroxy-2-oxo-3,9-dioxabicyclo[3.3.1]nonan-1-yl hexanoate:

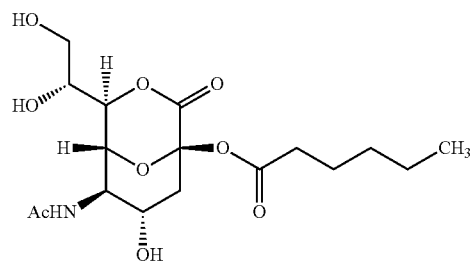 [SMILES: CCCCCC(=O)O[C@@]12C[C@H](O)[C@@H](NC(C)=O)[C@@H](O1)[C@@H]([C@H](O)CO)OC2=O]

Lactone C3: (1R,4R,5R,6R,7S)-6-acetomido-4[(R)-1,2-dihydroxyethyl]-7-hydroxy-2-oxo-3,9-dioxabicyclo[3.3.1]nonan-1-yl propionate:

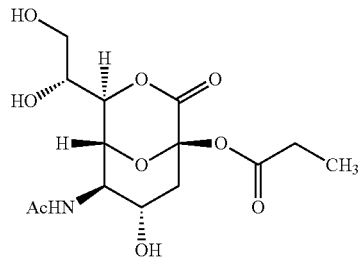 [SMILES: CCC(=O)O[C@@]12C[C@H](O)[C@@H](NC(C)=O)[C@@H](O1)[C@@H]([C@H](O)CO)OC2=O]

Lactone C9: (1R,4R,5R,6R,7S)-6-acetomido-4[(R)-1,2-dihydroxyethyl]-7-hydroxy-2-oxo-3,9-dioxabicyclo[3.3.1]nonan-1-yl nonanoate:

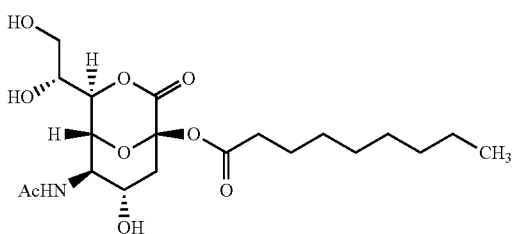 [SMILES: CCCCCCCCC(=O)O[C@@]12C[C@H](O)[C@@H](NC(C)=O)[C@@H](O1)[C@@H]([C@H](O)CO)OC2=O]

Fifteen (15) male Sprague-Dawley rats were assigned to 5 treatment groups (3 animals per group) that received either Sialic acid or Prodrugs at a dose level of 175 mg/kg. Each dose was given as a single oral gavage administration at a dose volume of 10 mL/kg. Blood samples for NANA and Prodrug analysis were collected at pre-dose (Day-2) and on the day of dosing at 5 min, 15 min, 30 min, 1 h, 2 h, 4 h, 8 h, 12 h and 24 h post dose. Data provided in FIGS. 3A-3D.

A second experiment was conducted with a different set of Prodrugs (Lactone C9, Lactone C12, and Lactone C16). Lactone C12 and Lactone C16 have the following structures:

Lactone C12: (1R,4R,5R,6R,7S)-6-acetomido-4[(R)-1,2-dihydroxyethyl]-7-hydroxy-2-oxo-3,9-dioxabicyclo[3.3.1]nonan-1-yl dodeconoate:

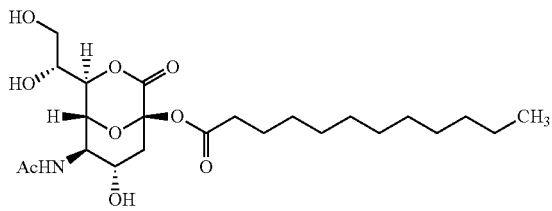 [SMILES: CCCCCCCCCCCC(=O)O[C@@]12C[C@H](O)[C@@H](NC(C)=O)[C@@H](O1)[C@@H]([C@H](O)CO)OC2=O]

Lactone C16: (1R,4R,5R,6R,7S)-6-acetomido-4[(R)-1,2-dihydroxyethyl]-7-hydroxy-2-oxo-3,9-dioxabicyclo[3.3.1]nonan-1-yl palmitate:

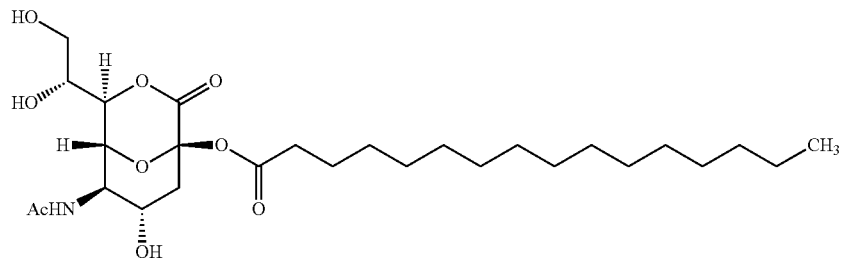 [SMILES: CCCCCCCCCCCCCCCC(=O)O[C@@]12C[C@H](O)[C@@H](NC(C)=O)[C@@H](O1)[C@@H]([C@H](O)CO)OC2=O]

Twelve (12) male Sprague-Dawley rats were assigned to 4 treatment groups (3 animals per group) that received either Sialic acid or Prodrugs at a dose level of 200 mg/kg. Each dose was given as a single oral gavage administration at a dose volume of 10 mL/kg. Blood samples for NANA and Prodrug analysis were collected at pre-dose (Day-2) and on the day of dosing at 5 min, 15 min, 30 min, 1 h, 2 h, 4 h, 8 h, 12 h and 24 h post dose. Data provided in FIGS. 4A-4D. Without being bound by theory, it is proposed that the prolonged PK curves show how the fatty acid is delaying clearance for the sialic lactone.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings.

What is claimed is:

1. A compound having structural Formula (Ia):

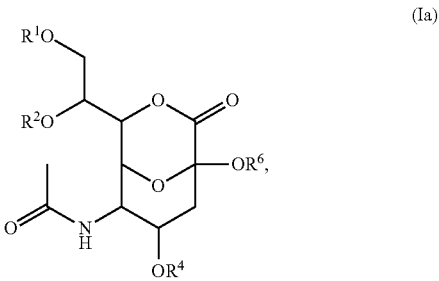

or a pharmaceutically acceptable salt or solvate thereof;

wherein:

$R^1$, $R^2$, and $R^4$ are independently hydrogen or a moiety selected from structural formula (a), (b), (c), (f), and (g):

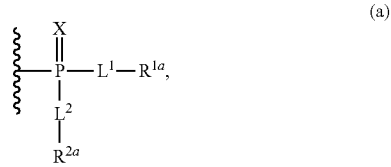

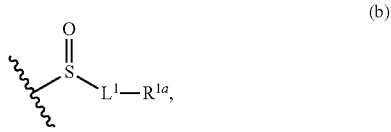

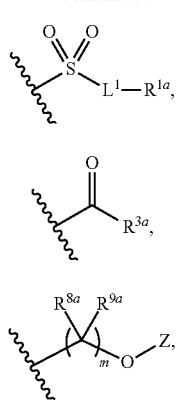

wherein $R^{3a}$ is optionally substituted alkyl;
$R^6$ is structural formula (f), wherein $R^{3a}$ is optionally substituted $C_5$-$C_{20}$ alkyl;
X is oxygen or sulfur;
$L^1$ and $L^2$ are each independently a covalent bond, —O—, or —$NR^{10a}$—;
$R^{10a}$ is hydrogen or optionally substituted alkyl;
$R^{1a}$ and $R^{2a}$ are each independently hydrogen, optionally substituted alkyl, optionally substituted heteroalkyl, optionally substituted aryl, optionally substituted heteroaryl, optionally substituted carbocyclyl, optionally substituted heterocyclyl, —$X^a$—C(O)—O—$R^{11a}$, or —$X^a$—O—C(O)—O—$R^{11a}$;
$X^a$ is optionally substituted alkylene;
each $R^{11a}$ is independently hydrogen, optionally substituted alkyl, or optionally substituted heteroalkyl;
each $R_{8a}$ and $R^{9a}$ is independently hydrogen or optionally substituted alkyl;
m is 1 or 2; and
Z is hydrogen, lower alkyl, an amide group, a lactam group, an ester group, a lactone group, an urea group, a cyclic urea group, a carbonate group, a cyclic carbonate group, a carbamate group, a cyclic carbamate group, or a moiety selected from (a), (b), (c), and (f).

2. The compound of claim 1, wherein the compounds of Formula (Ia) has the structure of Formula (IIa):

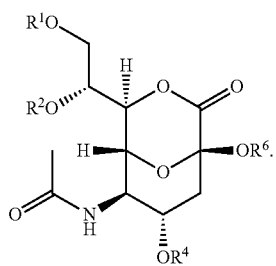

3. The compound of claim 1, wherein $R^{3a}$ in formula (f) of $R^6$ is $C_8$ alkyl.

4. The compound of claim 1, wherein $R^{3a}$ in formula (f) of $R^6$ is $C_{11}$ alkyl.

5. The compound of claim 1, wherein $R^{3a}$ in formula (f) of $R^6$ is $C_{15}$ alkyl.

6. A pharmaceutical composition comprising a compound of claim 1, or a pharmaceutically acceptable salt or solvate thereof, and a pharmaceutically acceptable carrier.

7. A sustained release pharmaceutical composition comprising a compound of claim 1, or a pharmaceutically acceptable salt or solvate thereof, wherein the release of the compound is over a period of about four hours or more.

8. A sustained release pharmaceutical composition comprising a compound of claim 1, or a pharmaceutically acceptable salt or solvate thereof, wherein the pharmacological effect from the compound lasts about four hours or more upon administration of the composition.

9. A sustained release pharmaceutical composition comprising a compound of claim 1, or a pharmaceutically acceptable salt or solvate thereof;
wherein the composition, upon administration, provides a therapeutically effective amount of the compound for about 4 hours or more.

10. A method for treating a sialic acid deficiency in a patient in need thereof comprising administering an effective amount of a compound of claim 1, or a pharmaceutically acceptable salt or solvate thereof.

11. The method of claim 10, wherein the sialic acid deficiency is myopathy associated with sialic acid deficiency.

12. The method of claim 11, wherein the myopathy associated with sialic acid deficiency is Hereditary Inclusion Body Myopathy (HIBM), Nonaka myopathy, or Distal Myopathy with Rimmed Vacuoles (DMRV).

13. A method for treating a sialic acid deficiency in a patient in need thereof comprising administering a compound of claim 1, or a pharmaceutically acceptable salt or solvate thereof wherein upon administration, the compound, or a pharmaceutically acceptable salt or solvate thereof, continuously provides a therapeutically effective amount of sialic acid for about 4 hours to about 24 hours.

14. The method of claim 13, wherein the sialic acid deficiency is myopathy associated with sialic acid deficiency.

15. The method of claim 14, wherein the myopathy associated with sialic acid deficiency is Hereditary Inclusion Body Myopathy (HIBM), Nonaka myopathy, or Distal Myopathy with Rimmed Vacuoles (DMRV).

* * * * *